(12) United States Patent
Chan et al.

(10) Patent No.: US 12,319,733 B2
(45) Date of Patent: Jun. 3, 2025

(54) THREONINE166 AND SERINE189 OF RUBICON RUN DOMAIN AS LRRK2 KINASE INHIBITION TARGET SITES

(71) Applicant: SINGAPORE HEALTH SERVICES PTE LTD, Singapore (SG)

(72) Inventors: Lai Ling Sharon Chan, Singapore (SG); Eng King Tan, Singapore (SG)

(73) Assignee: SINGAPORE HEALTH SERVICES PTE LTD, Singapore (SG)

( * ) Notice: Subject to any disclaimer, the term of this patent is extended or adjusted under 35 U.S.C. 154(b) by 940 days.

(21) Appl. No.: 17/436,951

(22) PCT Filed: Mar. 6, 2020

(86) PCT No.: PCT/SG2020/050113
§ 371 (c)(1),
(2) Date: Sep. 7, 2021

(87) PCT Pub. No.: WO2020/180257
PCT Pub. Date: Sep. 10, 2020

(65) Prior Publication Data
US 2022/0169720 A1    Jun. 2, 2022

(30) Foreign Application Priority Data

Mar. 7, 2019    (SG) .......................... 10201902046S

(51) Int. Cl.
| | | |
|---|---|---|
| *C07K 16/28* | (2006.01) | |
| *A61K 39/00* | (2006.01) | |
| *A61P 25/16* | (2006.01) | |
| *G01N 33/573* | (2006.01) | |
| *G01N 33/68* | (2006.01) | |

(52) U.S. Cl.
CPC .............. *C07K 16/28* (2013.01); *A61P 25/16* (2018.01); *G01N 33/573* (2013.01); *G01N 33/6896* (2013.01); *A61K 39/00* (2013.01); *C07K 2317/24* (2013.01); *C07K 2317/565* (2013.01); *G01N 2800/2835* (2013.01)

(58) Field of Classification Search
CPC .............. C07K 16/28; C07K 2317/24; C07K 2317/565; C07K 16/44; A61P 25/16; G01N 33/573; G01N 33/6896; G01N 2800/2835; G01N 2440/14; A61K 39/00; C12Q 1/485

See application file for complete search history.

(56) References Cited

FOREIGN PATENT DOCUMENTS

| | | | |
|---|---|---|---|
| CN | 112512584 | A  | 3/2021 |
| WO | 2010030936 | A2 | 3/2010 |
| WO | 2010064250 | A1 | 6/2010 |
| WO | 2014046966 | A1 | 3/2014 |

OTHER PUBLICATIONS

Gillardon et al. ATP-competitive LRRK2 inhibitors interfere with monoclonal antibody binding to the kinase domain of LRRK2 under native conditions. A method to directly monitor the active conformation of LRRK2? J Neurosci Methods. Mar. 30, 2013;214(1):62-8. (Year: 2013).*
Buus et al. High-resolution mapping of linear antibody epitopes using ultrahigh-density peptide microarrays. Mol Cell Proteomics. Dec. 2012;11(12):1790-800. (Year: 2012).*
Beiboer et al. Guided selection of a pan carcinoma specific antibody reveals similar binding characteristics yet structural divergence between the original murine antibody and its human equivalent. J Mol Biol. Feb. 25, 2000;296(3):833-49. (Year: 2000).*
Klimka et al. Human anti-CD30 recombinant antibodies by guided phage antibody selection using cell panning. Br J Cancer 83, 252-260 (2000). (Year: 2000).*
Griffiths et al. Human anti-self antibodies with high specificity from phage display libraries. EMBO J. Feb. 1993;12(2):725-34 (Year: 1993).*
Choi et al. Predicting antibody complementarity determining region structures without classification. Mol. BioSyst., 2011,7, 3327-3334 (Year: 2011).*
Barthelemy et al. Comprehensive analysis of the factors contributing to the stability and solubility of autonomous human VH domains. J Biol Chem. Feb. 8, 2008;283(6):3639-3654. (Year: 2008).*
Ward et al. Binding activities of a repertoire of single immunoglobulin variable domains secreted from *Escherichia coli*. Nature. Oct. 12, 1989;341(6242):544-6. (Year: 1989).*
De Genst et al. Antibody repertoire development in camelids. Dev Comp Immunol. 2006;30(1-2):187-98. (Year: 2006).*
Almagro et al. Humanization of antibodies. Front Biosci. Jan. 1, 2008;13:1619-33. (Year: 2008).*
Gershoni et al. Epitope mapping: the first step in developing epitope-based vaccines. BioDrugs. 2007;21(3):145-56. (Year: 2007).*
Blythe et al. Benchmarking B cell epitope prediction: underperformance of existing methods. Protein Sci. Jan. 2005;14(1):246-8. (Year: 2005).*
Schreiber et al. 3D-Epitope-Explorer (3DEX): localization of conformational epitopes within three-dimensional structures of proteins. J Comput Chem. Jul. 15, 2005;26(9):879-87. (Year: 2005).*
Ladner RC. Mapping the epitopes of antibodies. Biotechnol Genet Eng Rev. 2007;24:1-30. (Year: 2007).*
Dondelinger et al. Understanding the Significance and Implications of Antibody Numbering and Antigen-Binding Surface/Residue Definition. Front Immunol. Oct. 16, 2018;9:2278. (Year: 2018).*
Lin et al. Improved affinity of a chicken single-chain antibody to avian infectious bronchitis virus by site-directed mutagenesis of complementarity-determining region H3. 2011. African Journal of Biotechnology, 10(79):18294-18302. (Year: 2011).*

(Continued)

*Primary Examiner* — Anand U Desai
*Assistant Examiner* — Amber K Faust
(74) *Attorney, Agent, or Firm* — JCIP; Joseph G. Chu

(57) ABSTRACT

Method of detecting phosphorylation at Threonine 166 of a Rubicon protein to identify a subject having a disease associated with Leucine-rich repeat kinase 2 (LRRK2) such as Parkinson's disease and compounds and methods for treating the same.

20 Claims, 8 Drawing Sheets

Figure 1:
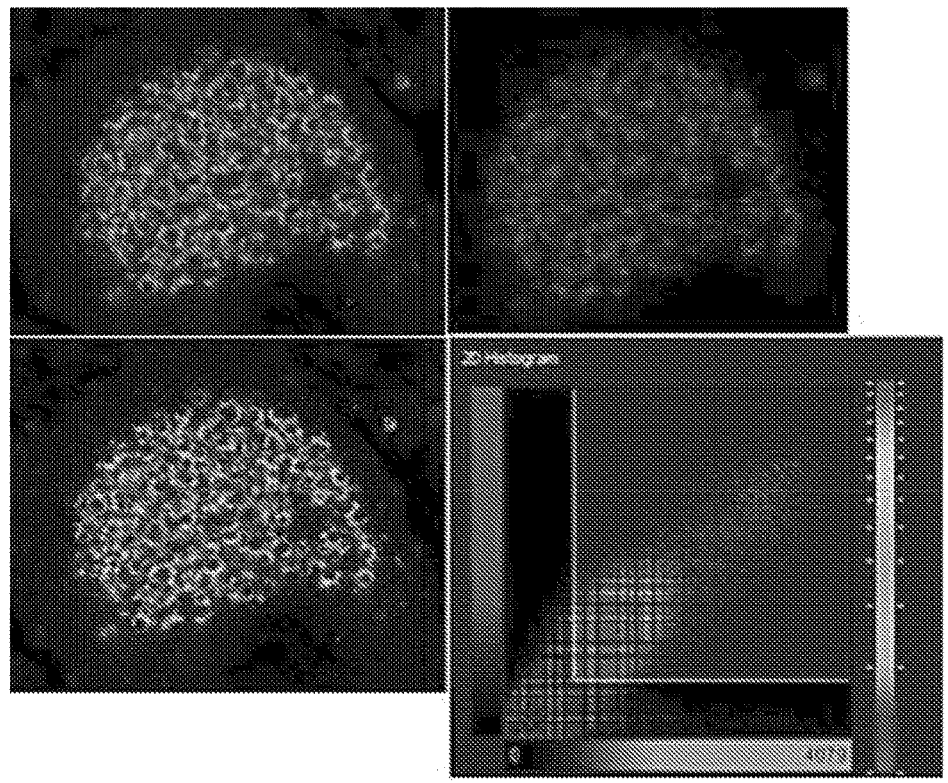

Specification includes a Sequence Listing.

(56) References Cited

OTHER PUBLICATIONS

Grønborg et al. A mass spectrometry-based proteomic approach for identification of serine/threonine-phosphorylated proteins by enrichment with phospho-specific antibodies: identification of a novel protein, Frigg, as a protein kinase A substrate. Mol Cell Proteomics. Jul. 2002;1(7):517-27. (Year: 2002).*

Extended European Search Report dated Dec. 9, 2022 for EP Application No. 20766522.5.

Esteves A R et al: "The Upshot of LRRK2 Inhibition to Parkinson's Disease Paradigm", Molecular Neurobiology, Springer US, New York, vol. 52, No. 3, Nov. 15, 2014 (Nov. 15, 2014), pp. 1804-1820, XP036181657, ISSN: 0893-7648, DOI: 10.1007/S12035-014-8980-6 [retrieved on Nov. 15, 2014] * the whole document *.

Pepperberg Irene M.: "Avian cognition and social interaction : Fifty years of advances", Interaction Studies Social Behaviour and Communication in Biological and Artificial Systems, vol. 12, No. 2, Aug. 1, 2011 (Aug. 1, 2011), pp. 195-207, XP093003388, ISSN: 1572-0373, DOI: 10.1075/is.12.2.0lpep Retrieved from the Internet: URL:http://dx.dol.org/10.1075/is.12.2.0lpeP> * the whole document*.

Kyle B. Fraser et al., Urinary LRRK2 phosphorylation predicts parkinsonian phenotypes in G2019S LRRK2 carriers, Neurology Mar. 15, 2016, vol. 86, (11):994-999 DOI: 10.1212/WNL.0000000000002436.

Claudia Manzoni et al.,mTOR independent regulation of macroautophagy by Leucine Rich Repeat Kinase 2 via Beclin-1, Scientific Reports, vol. 6, 1-10, Oct. 12, 2016:6:35106. doi: 10.1038/srep35106.

Chinese Office Action with Search Report Dated Mar. 22, 2024 for Chinese Application No. 202080028472.1.

Hartlova, A. et al., LRRK2 is a negative regulator of Mycobacterium tuberculosis phagosome maturation in macrophages. The EMBO Journal, May 22, 2018, vol. 37, No. 12, pp. e98694: 1-17 [Retrieved on Jun. 3, 2020] <DOI: 10.15252/EMBJ.201798694> Whole document, particularly Materials and Methods; Results.

Sun, Q. et al., The RUN Domain of Rubicon Is Important for hVps34 Binding, Lipid Kinase Inhibition, and Autophagy Suppression. The Journal of Biological Chemistry, Dec. 9, 2010, vol. 286, No. 1, pp. 185-191 [Retrieved on Jun. 3, 2020] <DOI: 10.1074/JBC.M110.126425> Whole document, particularly Experimental Procedures.

Matsunaga, K. et al., Two Beclin 1-binding Proteins, Atg14L and Rubicon, Reciprocally Regulate Autophagy at Different Stages. Nat Cell Biol., Mar. 8, 2009, vol. 11, No. 4, pp. 285-396 [Retrieved on Jun. 3, 2020] <DOI: 10.1091/MBC.E10-06-0495> Whole document, particularly "Antibodies and reagents" in Supplementary Methods.

Zhong, Y. et al., Distinct regulation of autophagic activity by Atg14L and Rubicon associated with Beclin 1-phosphatidylinositol-3-kinase complex. Nature Cell Biology, Mar. 8, 2009, vol. 11, pp. 468-476 [Retrieved on Jun. 3, 2020] <DOI: 10.1038/NCB1854> Whole document, particularly "Reagents and antibodies" in Supplementary Information.

International Search Report and Written Opinion of International Searching Authority for International Application No. PCT/SG2020/050113.

* cited by examiner

Figure 2
LRRK2 substrate kinase assay
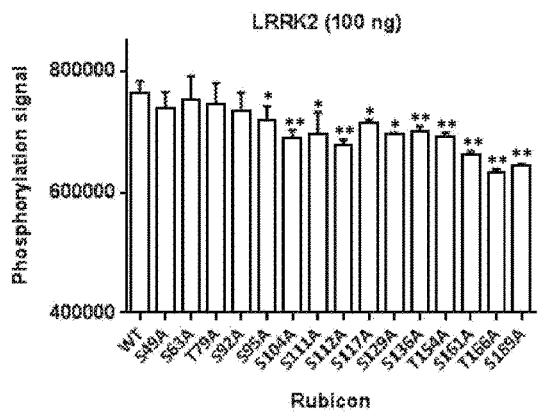
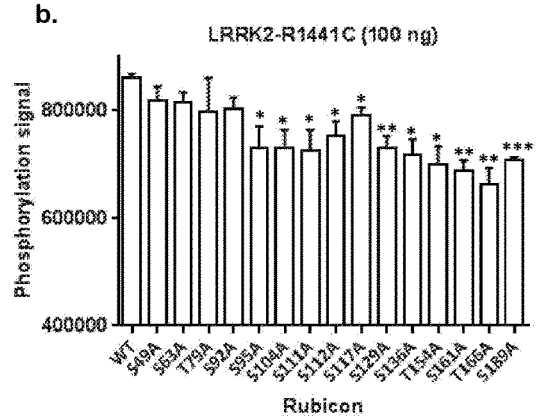
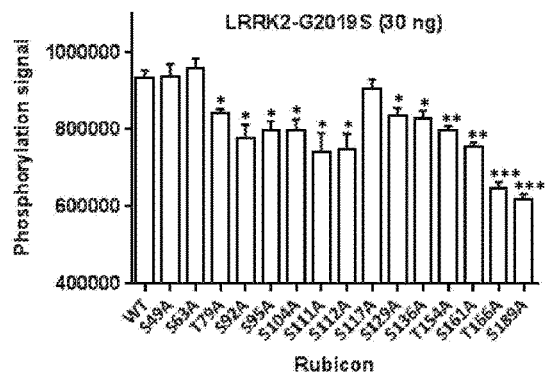
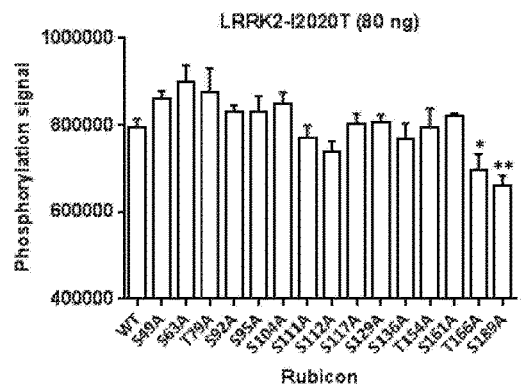
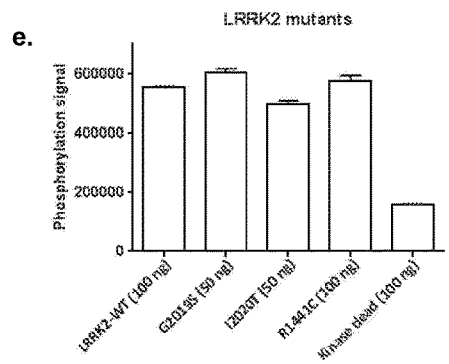

Figure 3
a. LRRK2 ADP Kinase Assay
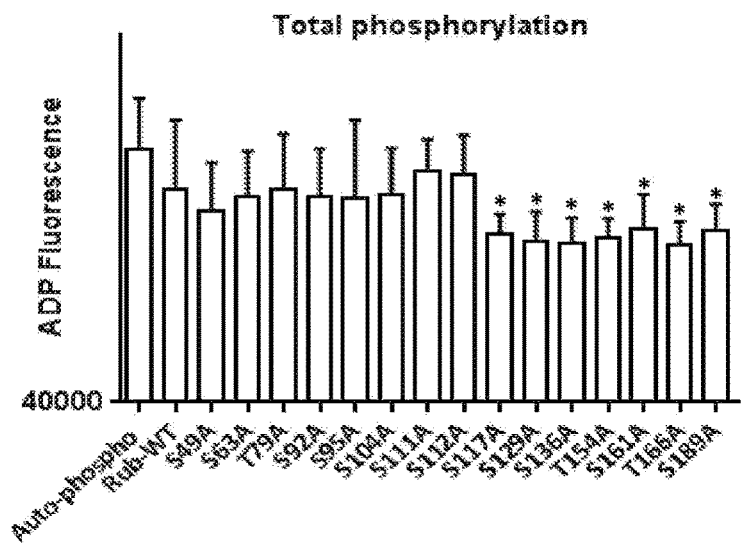
b. LRRK2 knockdown or over-expression in human neuronal cells.
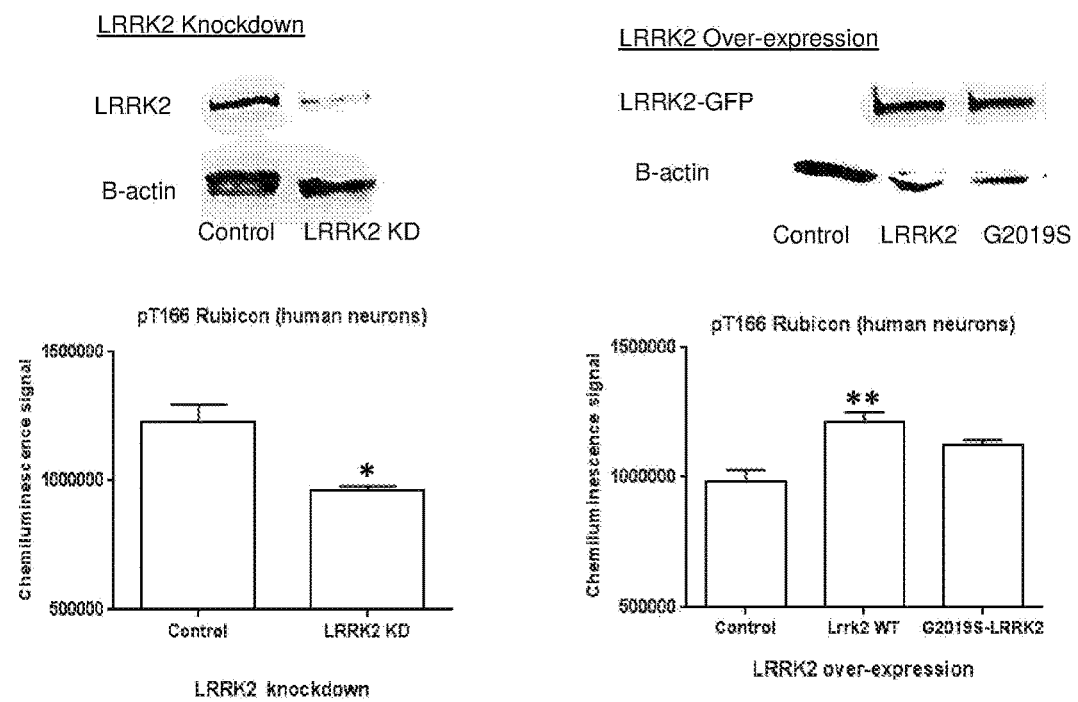

Figure 8
a. Endogenous protein expression
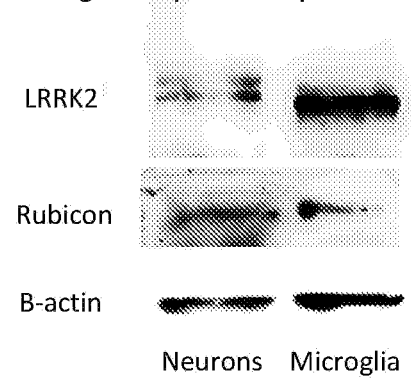
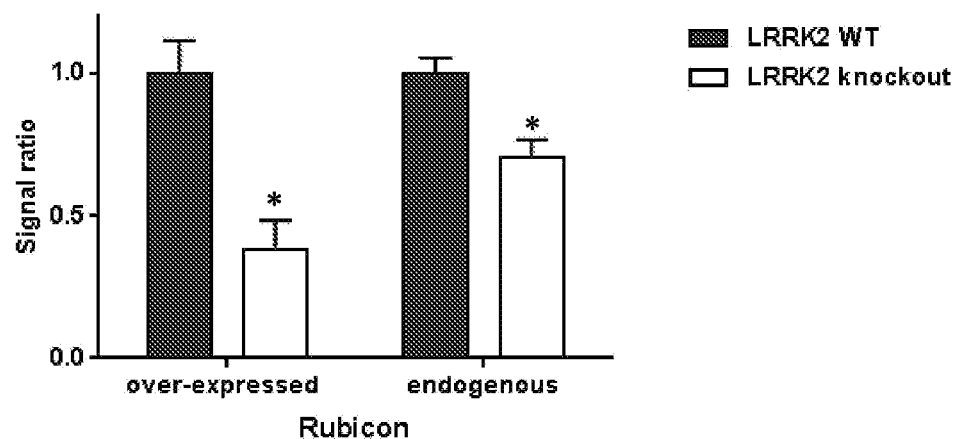

＃ THREONINE166 AND SERINE189 OF RUBICON RUN DOMAIN AS LRRK2 KINASE INHIBITION TARGET SITES

CROSS REFERENCE TO RELATED APPLICATIONS

This application claims the priority to Singapore patent application No. 10201902046S, filed 7 Mar. 2019, the contents of which are incorporated herein by reference.

FIELD

The present disclosure relates generally to methods antibodies, inhibitors and kits for diagnosing and/or providing treatments for diseases associated with Leucine-rich repeat kinase 2 (LRRK2) in particular diagnosing and/or providing treatments for Parkinson's disease (PD).

BACKGROUND

The following discussion of the background to the invention is intended to facilitate an understanding of the present invention only. It should be appreciated that the discussion is not an acknowledgement or admission that any of the material referred to was published, known or part of the common general knowledge of the person skilled in the art in any jurisdiction as at the priority date of the invention.

Leucine-rich repeat kinase 2 (LRRK2) is a serine/threonine kinase. Mutations in LRRK2 are associated with PD, chronic inflammation, such a Crohn's disease and mycobacterial infections. Mutations in LRRK2 are the most common cause of autosomal-dominant and sporadic PD accounting for up to 40% of PD cases in some populations. G2019S is the most prevalent LRRK2 mutant and is reported to exhibit enhanced kinase activity compared to wild-type LRRK2. Asian LRRK2 variants like N551 K, R1398H, R1628P and G2385R have been reported, though the functional impact of mutations are unknown as these variants have yet to be fully characterised. Familial LRRK2-linked PD has substantial overlap with idiopathic PD, suggesting that elucidating LRRK2 function may provide insights into both familial and idiopathic PD. Though LRRK2-linked toxicity has been associated with its kinase function, its physiological function remains unknown due to the lack of bona fide LRRK2 substrates. As a result, the quest for LRRK2 substrates and the development of LRRK2 kinase inhibitors has garnered interest as they may lead to therapeutic interventions for LRRK2-linked diseases like PD.

PD is a long-term degenerative disorder of the central nervous system and it primarily affects the motor system. PD is a global disease with no cure and treatment is mainly directed to improving symptoms. To date, there is no diagnostic assay to aid in the clinical diagnosis of PD. Current PD clinical diagnosis relies on motor symptoms and brain scans.

RUN domain protein as Beclin-1 interacting and cysteine-rich containing (Rubicon) is a protein known to be involved in autophagy, phagocytosis and immune responses.

There is a need to ameliorate at least some of the difficulties in diagnosing and/or providing treatments for Parkinson's disease.

SUMMARY

It is envisioned that the methods, antibodies, inhibitors and kits described will be useful for diagnosing and/or providing treatments for diseases associated with Leucine-rich repeat kinase 2 (LRRK2), in particular diagnosing and/or providing treatments for Parkinson's disease (PD).

Accordingly an aspect of the invention provides an in vitro method of detecting phosphorylation of a Rubicon protein comprising: isolating proteins from a sample; contacting the isolated proteins with an antibody that hybridises to a phosphorylated Threonine at 166 of a Rubicon protein to form a complex; detecting the complex wherein detection of the complex that varies from a predetermined value indicates that the sample comes from a subject having a disease associated with Leucine-rich repeat kinase 2 (LRRK2).

Another aspect of the invention provides an antibody which is capable of binding to Rubicon phosphorylated at Threonine 166.

Another aspect of the invention provides an antibody as described herein above for use in the diagnosis or treatment of a disease associated with Leucine-rich repeat kinase 2 (LRRK2).

Another aspect of the invention provides an inhibitor of Rubicon interaction with Leucine-rich repeat kinase 2 (LRRK2) comprising a compound able to block interaction of LRRK2 with Threonine 166 of the Rubicon protein.

Another aspect of the invention provides an inhibitor as described herein above for use in the treatment of a disease associated with Leucine-rich repeat kinase 2 (LRRK2).

Another aspect of the invention provides use of an antibody as described herein above or an inhibitor as described herein above in the manufacture of a medicament for the treatment of a disease associated with Leucine-rich repeat kinase 2 (LRRK2).

Another aspect of the invention provides a method of treating a subject in need having a disease associated with Leucine-rich repeat kinase 2 (LRRK2) comprising: administering a compound able to block interaction of LRRK2 with Threonine 166 and/or Serine 189 of the Rubicon protein.

Another aspect of the invention provides a kit comprising an antibody described herein above or an inhibitor described herein above, and detection reagents for detecting a disease associated with Leucine-rich repeat kinase 2 (LRRK2).

Other aspects and features of the present invention will become apparent to those of ordinary skill in the art upon review of the following description of specific embodiments of the invention in conjunction with the accompanying figures.

BREIF DESCRIPTION OF THE DRAWINGS

In the figures, which illustrate, by way of non-limiting examples only, embodiments of the present invention may include, FIG. 1. LRRK2 and Rubicon interaction. (a) LRRK2 and Rubicon co-localisation in post-mortem human PD brain. Post-mortem human substantia nigra brain tissue was stained for endogenous LRRK2 and Rubicon expression. Confocal images were analysed by Imaris software to generate 2D histogram and co-localisation statistics (Table 1). (b) Co-immunoprecipitation of LRRK2 and Rubicon. Co-immunoprecipitation was carried out with HEK lysates over-expressing human LRRK2-GFP and/or Rubicon-Flag.

FIG. 2(a)-2(e). Identification of LRRK2-specific Rubicon phosphosite. Wild-type or mutant LRRK2 kinase assay was carried out with wild-type or phosphor-null mutant Rubicon as substrate. Resultant phosphorylated Rubicon signal was tabulated as bar graphs and statistical significance was calculated using the Student's t-test against wild-type Rubicon. $*p<0.05$, $p<0.01$, $*p<0.001$.

FIG. 3. Validation of LRRK2-specific Rubicon phosphosite. (a) LRRK2 ADP kinase assay carried out with wild-type or phosphor-null mutant Rubicon as substrate measured generated ADP from the kinase reaction. Statistical significance was calculated using the Student's t-test against wild-type Rubicon; $*p<0.05$. (b) Human neuronal cells with endogenous LRRK2 knocked down or over-expressed LRRK2 were analysed for endogenous pT166 Rubicon expression using ELISA. Statistical significance was calculated using the Student's t-test against control and $*p<0.05$, $**p<0.01$.

FIG. 4(a)-4(f). Drosophila climbing assay and lifespan studies. Drosophila over-expressing human LRRK2±Rubicon were assessed for their climbing ability and their lifespan. Climbing assay was carried out every 10 days till Day 60 and the resultant climbing index was tabulated. Lifespan study was documented every seven days until all the flies have died. The last day for each drosophila line is labelled above the bar graph. Statistical analysis was carried out using multiple comparison with Tukey-Kramer post-hoc test. $*p<0.05$, $***p<0.001$ (Tables 2 and 3).

FIG. 5(a)-5(e). Drosophila tyrosine hydroxylase (TH) expression. Aged transgenic fly brains were stained for TH-positive neuronal clusters in five regions (PPL1, PPL2, PPM1/2, PPM3, PAL) and counted. Resultant count was tabulated and statistical significance was analysed using the Student's T-test after adjusting for multiple comparisons (Table 4).

Figure 6:
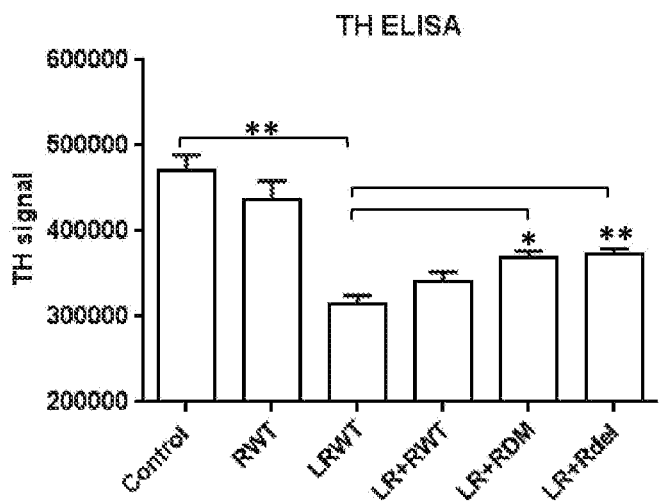

FIG. 6. Drosophila tyrosine hydroxylase (TH) expression. Aged fly brain lysates were analysed by TH ELISA and statistical significance was carried out using the Student's t-test where $*p<0.05$ and $**p<0.01$.

Figure 7:
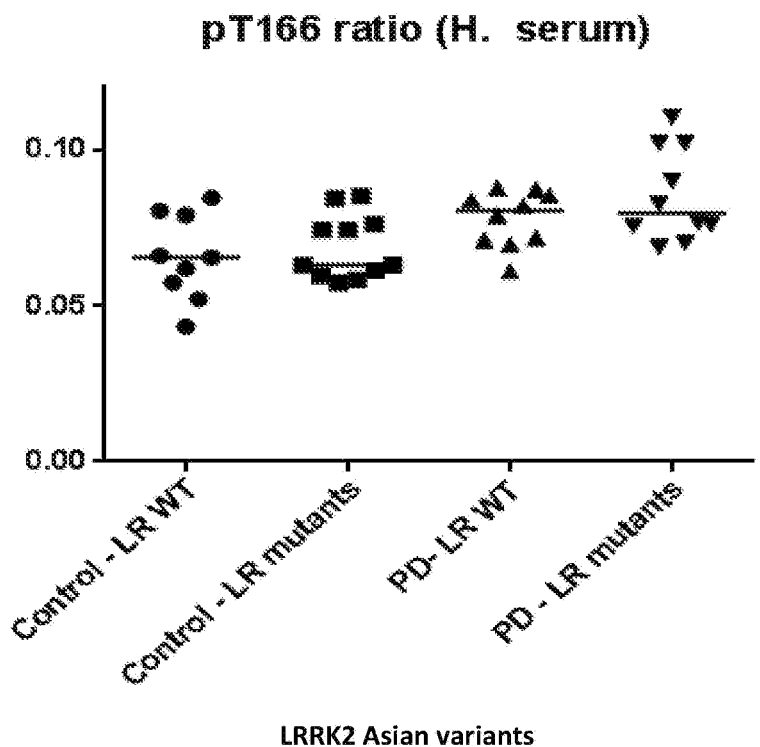

FIG. 7. Validation of pT166 Rubicon sandwich ELISA using human serum samples. Human serum from a local PD cohort harbouring LRRK2 variant mutations were analysed by pT166 Rubicon sandwich ELISA. 10 samples in each category represented as a dot plot with their respective median. Statistical significance was analysed using the Mann-Whitney test and significant numbers where $p<0.05$ are depicted in bold (Table 5).

FIG. 8. LRRK2 and Rubicon endogenous expression in microglia and macrophages. (a) Endogenous protein expression of LRRK2 and Rubicon in human neuronal cells and microglia. (b) Rubicon was over-expressed in mouse macrophages and cell lysates were analysed by pT166 Rubicon sandwich ELISA. Statistical significance was analysed using multiple T-tests corrected for multiple comparisons using Holm-Sidak method. Statistical significance is achieved when $P<0.05$ (Table 6).

FIG. 9(a)-9(d). Validation of pT166 Rubicon sandwich ELISA using human brain samples. Co-localised LRRK2 and Rubicon staining in human post-mortem substantia nigra brain sections of an aged-match non-PD brain (left) and PD brain (right). Post-mortem human brain samples were analysed by pT166 Rubicon sandwich ELISA. Human brain tissues were homogenised and fractionated into soluble and membrane-associated proteins. There were four samples in each category and their respective mean is represented as bar graphs. Statistical significance was analysed using one-way ANOVA and statistical significance is achieved when $P<0.05$ (Table 7).

DETAILED DESCRIPTION

Throughout this document, unless otherwise indicated to the contrary, the terms "comprising", "consisting of", "having" and the like, are to be construed as non-exhaustive, or in other words, as meaning "including, but not limited to".

Furthermore, throughout the document, unless the context requires otherwise, the word "include" or variations such as "includes" or "including" will be understood to imply the inclusion of a stated integer or group of integers but not the exclusion of any other integer or group of integers.

Unless defined otherwise, all other technical and scientific terms used herein have the same meaning as is commonly understood by a skilled person to which the subject matter herein belongs.

It was observed that LRRK2 kinase interacts with Rubicon RUN domain. LRRK2 is a serine/threonine kinase and Rubicon RUN domain contains 12 serine residues and three threonine residues. Rubicon phosphor-null mutants where a single serine/threonine residue was substituted with alanine were cloned to delineate RUN domain residues that are critical to LRRK2 function. LRRK2 kinase assays utilising wild-type or mutant LRRK2 were used to methodically screen for LRRK2-specific phosphosites. The consensus Rubicon phosphosites identified were threonine 166 (T166) and serine 189 (S189). If Rubicon mediates LRRK2-induced toxicity via LRRK2 kinase activity, then Rubicon phosphor-null mutants T166A and/or S189A will rescue LRRK2-induced toxicity.

Identifying LRRK2 substrates is key to elucidate the physiological function of LRRK2. Here, a novel LRRK2 substrate being Rubicon is reported and LRRK2-specific phosphosites are identified.

Accordingly, in various embodiments, an in vitro method of detecting phosphorylation of a Rubicon protein comprising: isolating proteins from a sample; contacting the isolated proteins with an antibody that hybridises to a phosphorylated Threonine at 166 of a Rubicon protein to form a complex; detecting the complex wherein detection of the complex that varies from a predetermined value indicates that the sample comes from a subject having a disease associated with Leucine-rich repeat kinase 2 (LRRK2).

The availability of a diagnostic assay that can be quantified and be easily carried out with minimal patient sample will enhance PD clinical diagnosis with added certainty. In various embodiments the use of sensitive ELISA detection is easily implemented in clinical settings. In various embodiments the use of blood samples such as serum samples or monocyte fraction samples further enhances the ease of implementation in clinical settings.

As used herein the term "sample" refers to a sample obtained from a subject such as an animal or a patient. In various embodiments the sample is obtained from a patient, and may be e.g. a blood, fluid or tissue sample. In various embodiments the sample is a blood or blood-derived sample. That is, the sample may be whole blood obtained from the patient, or may be derived from a quantity of blood obtained from the patient. In some embodiments, a blood derived sample may be quantity of blood plasma or serum derived from the subject's blood. In some embodiments, a blood derived sample may be quantity of monocyte fractions or patient-derived macrophage cell lines derived from the subject's blood.

In various embodiments the sample may be lung fluid. In various embodiments the sample may be tissue such as lung tissue, gastrointestinal tissue or brain tissue. In various embodiments the sample may be brain tissue.

In various embodiments, a sample is obtained from the patient suspected of having a disease associated with Leucine-rich repeat kinase 2 (LRRK2). In various embodiments, diseases associated with Leucine-rich repeat kinase 2

(LRRK2) include but are not limited to Parkinson's disease (PD), chronic inflammation, such a Crohn's disease and mycobacterial infections such as tuberculosis.

In various embodiments the methods comprise a step of obtaining a sample from the subject. In various embodiments the sample may be obtained and then stored, e.g. at −80° C. The stored sample can be thawed and analysed in accordance with the methods of the invention.

In various embodiments, a sample is obtained from the patient at a pre-determined time point in relation to a proposed or contemporaneous course of treatment of the disease associated with Leucine-rich repeat kinase 2 (LRRK2). In various embodiments samples are obtained from the patient at more than one time point in relation to a proposed or contemporaneous course of treatment of the disease associated with Leucine-rich repeat kinase 2 (LRRK2).

In various embodiments the subject having a disease associated with Leucine-rich repeat kinase 2 (LRRK2) is treated with a compound able to block interaction of LRRK2 with Threonine 166 and/or Serine 189 of the Rubicon protein. Blocking the interaction prevents phosphorylation of Threonine 166 and/or Serine 189 of the Rubicon protein slowing the deterioration of motor skills and/or extending life span. In various embodiments the subject having a disease associated with Leucine-rich repeat kinase 2 (LRRK2) is treated with a compound able to block interaction of LRRK2 with a phosphorylated Threonine 166 of the Rubicon protein. Blocking the interaction after phosphorylation of Threonine 166 and/or Serine 189 of the Rubicon protein will also have the effect of slowing the deterioration of motor skills and/or extending life span. In various embodiments the compound comprises a treatment antibody. In various embodiments the treatment antibody is a monoclonal antibody. In various embodiments the treatment antibody is a chimeric humanised antibody. In various embodiments the subject having a disease associated with Leucine-rich repeat kinase 2 (LRRK2) is treated with a compound able to block interaction of LRRK2 with a phosphorylated Threonine 166 of the Rubicon protein.

In various embodiments the sample is or has been obtained from the patient up to 1 day, 2 days, 3 days, 4 days, 5 days, 6 days, 7 days, 8 days, 9 days, 10 days, 11 days, 12 days, 13 days, 2 weeks, 3 weeks, 4 weeks, 2 months, 3 months, 4 months, 5 months, 6 months or 1 year prior to a therapeutic intervention to treat the disease.

In various embodiments the sample is or has been obtained from the patient during the course of a therapeutic intervention to treat the disease. In various embodiments the sample is or has been obtained from the patient after commencement of a therapeutic intervention to treat the disease.

In various embodiments the sample is or has been obtained from the patient up to 1 day, 2 days, 3 days, 4 days, 5 days, 6 days, 7 days, 8 days, 9 days, 10 days, 11 days, 12 days, 13 days, 2 weeks, 3 weeks, 4 weeks, 2 months, 3 months, 4 months, 5 months, 6 months or 1 year after a therapeutic intervention to treat the disease (such as after commencement, i.e. first administration of, the therapeutic intervention). In various embodiments the sample is or has been obtained from the patient not more than 1 year, 6 months, 5 months, 4 months, 3 months, 2 months, 4 weeks, 3 weeks, 2 weeks, 13 days, 12 days, 11 days, 10 days, 9 days, 8 days, 7 days, 6 days, 5 days, 4 days, 3 days, 2 days or 1 day after a therapeutic intervention to treat the disease (such as after commencement, i.e. first administration of, the therapeutic intervention).

In various embodiments the sample is or has been obtained from the patient on or after completion of the course of a therapeutic intervention to treat the disease. In various embodiments the sample is or has been obtained from the patient up to 1 day, 2 days, 3 days, 4 days, 5 days, 6 days, 7 days, 8 days, 9 days, 10 days, 11 days, 12 days, 13 days, 2 weeks, 3 weeks, 4 weeks, 2 months, 3 months, 4 months, 5 months, 6 months or 1 year after completion of the course of a therapeutic intervention to treat the disease. In various embodiments the sample is or has been obtained from the patient not more than 1 year, 6 months, 5 months, 4 months, 3 months, 2 months, 4 weeks, 3 weeks, 2 weeks, 13 days, 12 days, 11 days, 10 days, 9 days, 8 days, 7 days, 6 days, 5 days, 4 days, 3 days, 2 days or 1 day after completion of the course of a therapeutic intervention to treat the disease. In various embodiments the sample is obtained from the patient post-mortem.

As used herein the term "Rubicon protein" refers to RUN domain protein as Beclin-1 interacting and cysteine-rich containing. In various embodiments the Rubicon protein has an amino acid sequence set forth in SEQ ID NO. 1 or functional variants thereof that retains one or more of the known functions of Rubicon such as interact with Beclin-1, interact with Vps34, interact with UVRAG, interact with Rab7 or inhibition of autophagy and involvement in phagocytosis and immune responses. A functional variant may have one or more substitution, deletion or additional amino acid to SEQ ID NO. 1 that retains one or more of the known functions of Rubicon. In various embodiments a functional variant comprise a sequence sharing 60%, or 70% or 80% or 90% or 95% or 96% or 97% or 98% or 99% sequence homology with SEQ ID NO. 1. As used herein Threonine at 166 refers to a Threonine in the 166th amino acid of SEQ ID NO. 1 or a Threonine somewhere in the vicinity of the 166th amino acid of a functional variant. Serine at 189 refers to a Serine in the 189th amino acid of SEQ ID NO. 1 or a Serine somewhere in the vicinity of the 189th amino acid of a functional variant.

As used herein the term "a disease associated with Leucine-rich repeat kinase 2 (LRRK2)" refers to any disease that has identified LRRK2 of SEQ ID NO. 3 as a risk factor. In various embodiments a disease associated with LRRK2 are selected from Parkinson's disease; chronic inflammation such as Crohn's disease or ulcerative colitis; and bacterial infections such as mycobacterial infections. In various embodiments a disease associated with LRRK2 is Parkinson's disease. In various embodiments the disease associated with LRRK2 may comprise an intact LRRK2 represented as the amino acid sequence set forth in SEQ ID NO. 3. In various other embodiments the disease associated with LRRK2 may comprise mutations including additions, deletions or substitutions within the LRRK2 protein of SEQ ID NO. 3.

In various embodiments the antibody is a monoclonal antibody. In various embodiments the antibody is a chimeric humanised antibody.

In various embodiments the antibody-Rubicon complex may be detected and/or measured by various methods well known in the art, for example by western blot, immunohistochemistry, immunocytochemistry, flow cytometry, ELISA, ELISPOT, reporter-based methods, etc. In various embodiments the antibody-Rubicon complex is detected with an enzyme linked immunosorbent assay (ELISA). In various embodiments, the ELISA detection may be via direct ELISA that permits calculation of the absolute amount. In various embodiments, the ELISA detection may be via indirect ELISA. In various embodiments, the ELISA detection may be via sandwich ELISA which may provide more specific quantification. In various embodiments, the ELISA detection may be via any method that allows detection of antibody-Rubicon complex.

In various embodiments, the predetermined value is the threshold for the normal range in a healthy individual that has no disease associated with Leucine-rich repeat kinase 2 (LRRK2) wherein variation from the predetermined value there is an indication that disease is present. In various embodiments, the predetermined value is a percentage, or a ratio of Rubicon protein phosphorylated at Threonine 166 of SEQ ID NO. 1 in relation to the total amount Rubicon protein in the sample. In various embodiments detection of the complex above a predetermined value indicates that the sample comes from a subject having a disease associated with Leucine-rich repeat kinase 2 (LRRK2). In various other embodiments, detection of the complex below a predetermined value indicates that the sample comes from a subject having a disease associated with Leucine-rich repeat kinase 2 (LRRK2).

In various embodiments, the in vitro method further comprises removing blocking proteins prior to contacting the isolated proteins with the antibody. In various embodiments the blocking protein may comprise albumin. In various embodiments the blocking protein may be removed by filtration, centrifugation, tagged precipitation or any method known in the art to remove specific proteins. Advantageously, the method is sensitive and specific enough to detect Rubicon protein phosphorylated at Threonine 166 in all blood samples. Generally, however, albumin removal from serum samples permits enhanced detection where serum samples are used.

In various embodiments, an antibody which is capable of binding to Rubicon phosphorylated at Threonine 166 is provided.

In various embodiments, the antibody comprises at least one variable region incorporating the CDR selected from amino acid sequences i) to vi):

```
i) LC-CDR1:
                                    (SEQ ID NO. 4)
RSSQSLVHSNGNTYLH;

ii) LC-CDR2:
                                    (SEQ ID NO. 5)
KLSNRFS;

iii) LC-CDR3:
                                    (SEQ ID NO. 6)
SQSTHVPLT;

iv) HC-CDR1:
                                    (SEQ ID NO. 7)
NYGVS;

v) HC-CDR2:
                                    (SEQ ID NO. 8)
TINSNGGSKYYPDSVKG;

vi) HC-CDR3:
                                    (SEQ ID NO. 9)
DVWLRRQWYFDV;
``` and a functional variant with 99% amino acid sequence identity to any one of amino acid sequences i) to vi).

In various embodiments, the antibody comprises amino acid sequences:

```
i) LC-CDR1:
                                    (SEQ ID NO. 4)
RSSQSLVHSNGNTYLH;

ii) LC-CDR2:
                                    (SEQ ID NO. 5)
KLSNRFS;

iii) LC-CDR3:
                                    (SEQ ID NO. 6)
SQSTHVPLT;

iv) HC-CDR1:
                                    (SEQ ID NO. 7)
NYGVS;

v) HC-CDR2:
                                    (SEQ ID NO. 8)
TINSNGGSKYYPDSVKG;

vi) HC-CDR3:
                                    (SEQ ID NO. 9)
DVWLRRQWYFDV;
``` or a functional variant with 99% amino acid sequence identity to any one of amino acid sequences i) to vi).

In various embodiments, the antibody comprises amino acid sequences set forth in SEQ ID NO. 12 and SEQ ID NO. 13 or a functional variant with 99% amino acid sequence identity to SEQ ID NO. 12 and SEQ ID NO. 13.

In various embodiments, the functional variant comprises an antibody that is capable of binding to Rubicon phosphorylated at Threonine 166 at a supernatant dilution of at least 1:30. In various embodiments, the functional variant comprises an antibody that is capable of binding to Rubicon phosphorylated at Threonine 166 at a supernatant dilution of at least 1:90. In various embodiments, the functional variant comprises an antibody that is capable of binding to Rubicon phosphorylated at Threonine 166 at a supernatant dilution of at least 1:270. In various embodiments, the functional variant comprises an antibody that is capable of binding to Rubicon phosphorylated at Threonine 166 at a supernatant dilution of at least 1:810. In various embodiments, the functional variant comprises an antibody that is capable of binding to Rubicon phosphorylated at Threonine 166 at a supernatant dilution of at least 1:2,430. In various embodiments, the functional variant comprises an antibody that is capable of binding to Rubicon phosphorylated at Threonine 166 at a supernatant dilution of between 1:8 and 1:2,500. In various embodiments, the functional variant comprises an antibody that is capable of binding to Rubicon phosphorylated at Threonine 166 at a supernatant dilution of between 1:10 and 1:2,500. In various embodiments, the functional variant comprises an antibody that is capable of binding to Rubicon phosphorylated at Threonine 166 at a supernatant dilution of between 1:20 and 1:2,500. In various embodiments, the functional variant comprises an antibody that is capable of binding to Rubicon phosphorylated at Threonine 166 at a supernatant dilution of between 1:80 and 1:2,500. In various embodiments, the functional variant comprises an antibody that is capable of binding to Rubicon phosphorylated at Threonine 166 at a supernatant dilution of between 1:250 and 1:2,500. In various embodiments, the functional variant comprises an antibody that is capable of binding to Rubicon phosphorylated at Threonine 166 at a supernatant dilution of between 1:800 and 1:2,500.

Polyclonal Antibodies

In various embodiments the antibody may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant.

Typically, the immunizing agent and/or adjuvant will be injected in the mammal by multiple subcutaneous or intraperitoneal injections. The intensity of the response is determined by several factors including the size of the immunogen molecule, its chemical characteristics, and how different it is from the animal's own proteins. Most natural immunogens are proteins with a molecular weight above 5 kDa that come from sources phylogenically far removed from the host animal (i.e., human proteins injected into rabbits or goats). It is desirable to use highly purified proteins as immunogens, since the animal will produce antibodies to even small amounts of impurities present as well as to the major component. The antibody response increases with repeated exposure to the immunogen, so a series of injections at regular intervals is needed to achieve both high levels of antibody production and antibodies of high affinity.

In various embodiments the antibody engages, hybridizes to or binds the Rubicon protein phosphorylated at Threonine 166. In various embodiments the antibody engages, hybridizes to or binds the Rubicon protein at Threonine 166. In various embodiments the antibody engages, hybridizes to or binds the Rubicon protein at phosphorylated Threonine 166. In various embodiments the amino acid sequence will be selected from the region of about 117 to 189 in the Rubicon protein. Sequences of at least 5, 6, 7, 8, 9, 10, 15, 20, 25, 30 amino acids from this region in SEQ ID NO. 1 will generally be used to generate those antibodies. In various embodiments the amino acid sequence is SEQ ID NO. 2. Desirably, the sequence selected will generate an antibody that specifically interferes with binding of Rubicon and LRRK2.

Not all immunogenic molecules will however generate the level of antibody desired. To increase the intensity of the immune response immunogens are combined with complex mixtures called adjuvants. Adjuvants are a mixture of natural or synthetic compounds that, when administered with antigens, enhance the immune response. Adjuvants are used to (1) stimulate an immune response to an antigen that is not inherently immunogenic, (2) increase the intensity of the immune response, (3) preferentially stimulate either a cellular or a humoral response (i.e., protection from disease versus antibody production). Examples of adjuvants which may be employed include Freund's complete adjuvant and MPL-TDM adjuvant (monophosphoryl Lipid A, synthetic trehalose dicorynomycolate).

If the immunogen is still unable to generate an acceptable response, it may be conjugated to a carrier protein that is more immunogenic. Small molecules such as drugs, organic compounds, and peptides and oligosaccharides with a molecular weight of less than 2-5 kDa like, for example, SEQ ID NO.: 2, are not usually immunogenic, even when administered in the presence of adjuvant. In order to generate an immune response to these compounds, it is necessary to attach them to a protein or other compound, termed a carrier that is immunogenic. When attached to a carrier protein the small molecule immunogen is called a hapten. Haptens are also conjugated to carrier proteins for use immunoassays. The carrier protein provides a means of attaching the hapten to a solid support such as a microtiter plate or nitrocellulose membrane. When attached to agarose they may be used for purification of the anti-hapten antibodies. They may also be used to create a multivalent antigen that will be able to form large antigen-antibody complexes. When choosing carrier proteins, remember that the animal will form antibodies to the carrier protein as well as to the attached hapten. It is therefore relevant to select a carrier protein for immunization that is unrelated to proteins that may be found in the assay sample. If haptens are being conjugated for both immunization and assay, the two carrier proteins should be as different as possible. This allows the antiserum to be used without having to isolate the anti-hapten antibodies from the anti-carrier antibodies.

In various embodiments the immunizing agent is SEQ ID NO. 2 conjugated to a protein known to be immunogenic in the mammal being immunized.

Examples of such immunogenic proteins include but are not limited to keyhole limpet hemocyanin (KLH), serum albumin, bovine thyroglobulin, soybean trypsin inhibitor, and a toxoid, for example tetanus toxoid.

KLH is a respiratory protein found in molluscs. Its large size makes it very immunogenic, and the large number of lysine residues available for conjugation make it very useful as a carrier for haptens. The phylogenic separation between mammals and molluscs increases the immunogenicity and reduces the risk of cross-reactivity between antibodies against the KLH carrier and naturally occurring proteins in mammalian samples.

KLH is offered both in its native form, for conjugation via amines, and succinylated, for conjugation via carboxyl groups. Succinylated KLH may be conjugated to a hapten containing amine groups (such as a peptide) via cross-linking with carbodiimide between the newly introduced carboxyl groups of KLH and the amine groups of the hapten. Protocols for conjugation of haptens to carrier proteins are known in the art.

The immunization protocol may be selected by one skilled in the art without undue experimentation. Protocols for preparing immunogens, immunization of animals, and collection of antiserum may be found in reference material available to a person skilled in the art.

Monoclonal Antibodies

In various embodiments the antibodies may, alternatively, be monoclonal antibodies. Monoclonal antibodies may be prepared using hybridoma methods, such as those described by Kohler and Milstein (1975), Nature, 256:495. In a hybridoma method, a mouse, hamster, or other appropriate host animal, is typically immunized with an immunizing agent as described above to elicit lymphocytes that produce or are capable of producing antibodies that will specifically bind to the immunizing agent. Alternatively, the lymphocytes may be immunized in vitro.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies.

The culture medium in which the hybridoma cells are cultured can then be assayed for the presence of monoclonal antibodies directed against Rubicon protein phosphorylated at Threonine 166.

After the desired hybridoma cells are identified, the clones may be subcloned by limiting dilution procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods known in the art.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

In vitro methods are also suitable for preparing monovalent antibodies. Digestion of antibodies to produce fragments thereof, particularly, Fab fragments, can be accomplished using routine techniques known in the art.

Human and Chimeric Humanized Antibodies

The antibodies of the invention may further comprise chimeric humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding sub-sequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the methods known in the art, by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Bispecific Antibodies

In various embodiment bispecific antibodies are monoclonal, preferably human or humanized, antibodies that have binding specificities for at least two different antigens. In the present case, one of the binding specificities is for Rubicon protein phosphorylated at Threonine 166, the other one is for another compound having Rubicon protein phosphorylated at Serine 189.

Methods for making bispecific antibodies are known in the art. Traditionally, the recombinant production of bispecific antibodies is based on the co-expression of two immunoglobulin heavy-chain/light-chain pairs, where the two heavy chains have different specificities.

In various embodiments, an antibody as described herein is provided for use in the treatment of a disease associated with Leucine-rich repeat kinase 2 (LRRK2).

As mentioned above, in various embodiments the term "a disease associated with Leucine-rich repeat kinase 2 (LRRK2)" refers to any disease that has identified LRRK2 of SEQ ID NO. 3 as a risk factor. In various embodiments a disease associated with LRRK2 are selected from Parkinson's disease; chronic inflammation such as Crohn's disease or ulcerative colitis; and bacterial infections such as mycobacterial infections. In various embodiments a disease associated with LRRK2 is Parkinson's disease.

In various embodiments the disease associated with Leucine-rich repeat kinase 2 (LRRK2) is Parkinson's disease.

In various embodiments, an inhibitor of Rubicon interaction with Leucine-rich repeat kinase 2 (LRRK2) comprising a compound able to block interaction of LRRK2 with Threonine 166 of the Rubicon protein is provided.

Current LRRK2 inhibitors directly targets LRRK2 kinase and cause adverse side effects when tested in in vivo models. Blocking or targeting specific phosphosites of LRRK2 substrate Rubicon protein has an indirect effect on the kinase. This exerts more control as the inhibition effects are confined to interactions between LRRK2 and Rubicon and pathways related to this interaction rather than affecting the generic function of LRRK2 alone.

In various embodiments the inhibitor compound comprises an antibody. In various embodiments the compound comprises a chimeric humanised antibody. In various embodiments the compound comprises a monoclonal antibody.

In various embodiments, an inhibitor as described herein above may be provided for use in the treatment of a disease associated with Leucine-rich repeat kinase 2 (LRRK2).

As mentioned above, in various embodiments the term "a disease associated with Leucine-rich repeat kinase 2 (LRRK2)" refers to any disease that has identified LRRK2 of SEQ ID NO. 3 as a risk factor. In various embodiments a disease associated with LRRK2 are selected from Parkinson's disease; chronic inflammation such as Crohn's disease or ulcerative colitis; and bacterial infections such as mycobacterial infections. In various embodiments the inhibitor is for use in the treatment of the disease associated with Leucine-rich repeat kinase 2 (LRRK2) being Parkinson's disease.

In various embodiments, use of an antibody as described herein above or an inhibitor as described herein above in the manufacture of a medicament for the treatment of a disease associated with Leucine-rich repeat kinase 2 (LRRK2).

As mentioned above, in various embodiments the term "a disease associated with Leucine-rich repeat kinase 2 (LRRK2)" refers to any disease that has identified LRRK2 of SEQ ID NO. 3 as a risk factor. In various embodiments a disease associated with LRRK2 are selected from Parkinson's disease; chronic inflammation such as Crohn's disease or ulcerative colitis; and bacterial infections such as mycobacterial infections. In various embodiments the use of the antibody or the inhibitor in the manufacture of a medicament for the treatment of a disease associated with Leucine-rich repeat kinase 2 (LRRK2) is for Parkinson's disease.

In various embodiments, a method of treating a subject in need having a disease associated with Leucine-rich repeat kinase 2 (LRRK2) comprising: administering a compound able to block interaction of LRRK2 with Threonine 166 and/or Serine 189 of the Rubicon protein.

In various embodiments, the compound is able to block interaction of LRRK2 with phosphorylated Threonine 166 and/or Serine 189 of the Rubicon protein. Blocking the interaction either before or after phosphorylation of Threonine 166 and/or Serine 189 of the Rubicon protein will have the effect of slowing the deterioration of motor skills and/or extending life span.

In various embodiments the compound used in the method comprises an antibody as described herein above. In various embodiments the antibody is a chimeric humanised antibody as described herein above. In various embodiments the antibody is a monoclonal antibody as described herein above.

In various embodiments, the compound is administered any suitable way known in the art. In various embodiments, the compound is administered by injection. In various embodiments, the compound is administered by direct injection to the site of interaction of LRRK2 with Threonine 166 and/or Serine 189 of the Rubicon protein that is responsible for causing the disease associated with Leucine-rich repeat kinase 2 (LRRK2).

In various embodiments, a kit comprising an antibody described herein above, and detection reagents for detecting a disease associated with Leucine-rich repeat kinase 2 (LRRK2) is provided.

In various embodiments the detection reagents are those used for an enzyme linked immunosorbent assay (ELISA). In various embodiments, the detection reagents are those used for direct ELISA. In various embodiments, the detection reagents are those used for indirect ELISA. In various embodiments, the detection reagents are those used for sandwich ELISA. In various embodiments, the detection reagents are those used for any method that allows detection of antibody-Rubicon complex. In various embodiments, depending on the method used the detection reagents may be selected from any one of: antigens to coat the microtiter plate; blocking reagents for unbound sites to prevent false positives; anti IgG conjugated enzymes; substrates that react with the enzyme to permit detection by colour change, fluorescence or any other means known in the art; additional reagents such as wash buffers, stop solutions, stabilizers; and any combination thereof.

In various embodiments, the kit may comprise a microtiter plate precoated with the antibodies described herein above. This will facilitate more rapid detection and reduce the chance of contamination.

As mentioned above, in various embodiments the term "a disease associated with Leucine-rich repeat kinase 2 (LRRK2)" refers to any disease that has identified LRRK2 of SEQ ID NO. 3 as a risk factor. In various embodiments a disease associated with LRRK2 are selected from Parkinson's disease; chronic inflammation such as Crohn's disease or ulcerative colitis; and bacterial infections such as mycobacterial infections.

In various embodiments the disease associated with Leucine-rich repeat kinase 2 (LRRK2) is Parkinson's disease.

EXAMPLES

Post-mortem human substantia nigra brain tissue was stained for endogenous LRRK2 (green fluorescence) and Rubicon (red fluorescence) expression. The extent of LRRK2 and Rubicon co-localisation (yellow fluorescence) was analysed by confocal microscopy and co-localisation statistics revealed a high degree of correlation between LRRK2 and Rubicon (FIG. 1, Table 1). LRRK2 and Rubicon interaction was confirmed by co-immunoprecipitation.

TABLE 1

Analysis of co-localization of LRRK2 and Rubicon

| Co-localization statistics | Value | Interpretation |
| --- | --- | --- |
| Pearson's coefficient | 0.7286 | Strong correlation |

Two methods of LRRK2 kinase assay was used to screen for Rubicon phosphor-null mutants. The first method quantified the extent of Rubicon phosphorylation by LRRK2 kinase and determined T166 and S189 as the consensus LRRK2-specific phosphosites (FIG. 2). The second method quantified the amount of generated ADP as a by-product of LRRK2 kinase activity and showed that Rubicon mutant's 117-189 amino acids significantly decreased LRRK2 kinase activity (FIG. 3a). Peptide analyses suggested that LRRK2 prefers threonine residue as a phosphorylation site, therefore a customised monoclonal antibody targeting phosphor-T166 (pT166) Rubicon was generated to verify the identified phosphosite. Human neurons with endogenous LRRK2 knocked down had a 32.4% decrease in pT166-Rubicon compared to control; human neurons transiently over-expressing wild-type (WT) LRRK2 or mutant LRRK2-G2019S had a 12% and 26% increase in pT166-Rubicon respectively compared to control (FIG. 3b).

Figure 4:
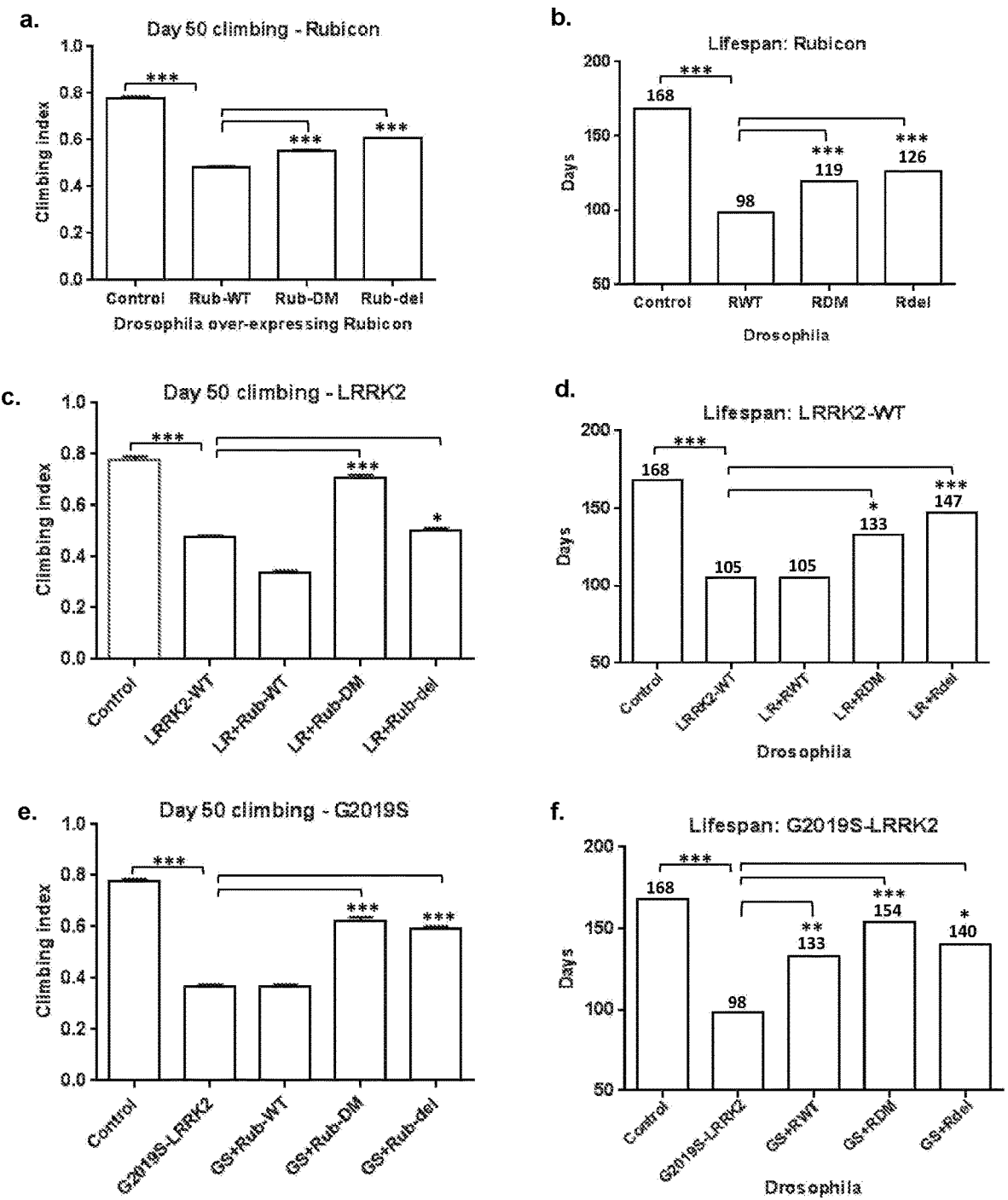
Figure 5:
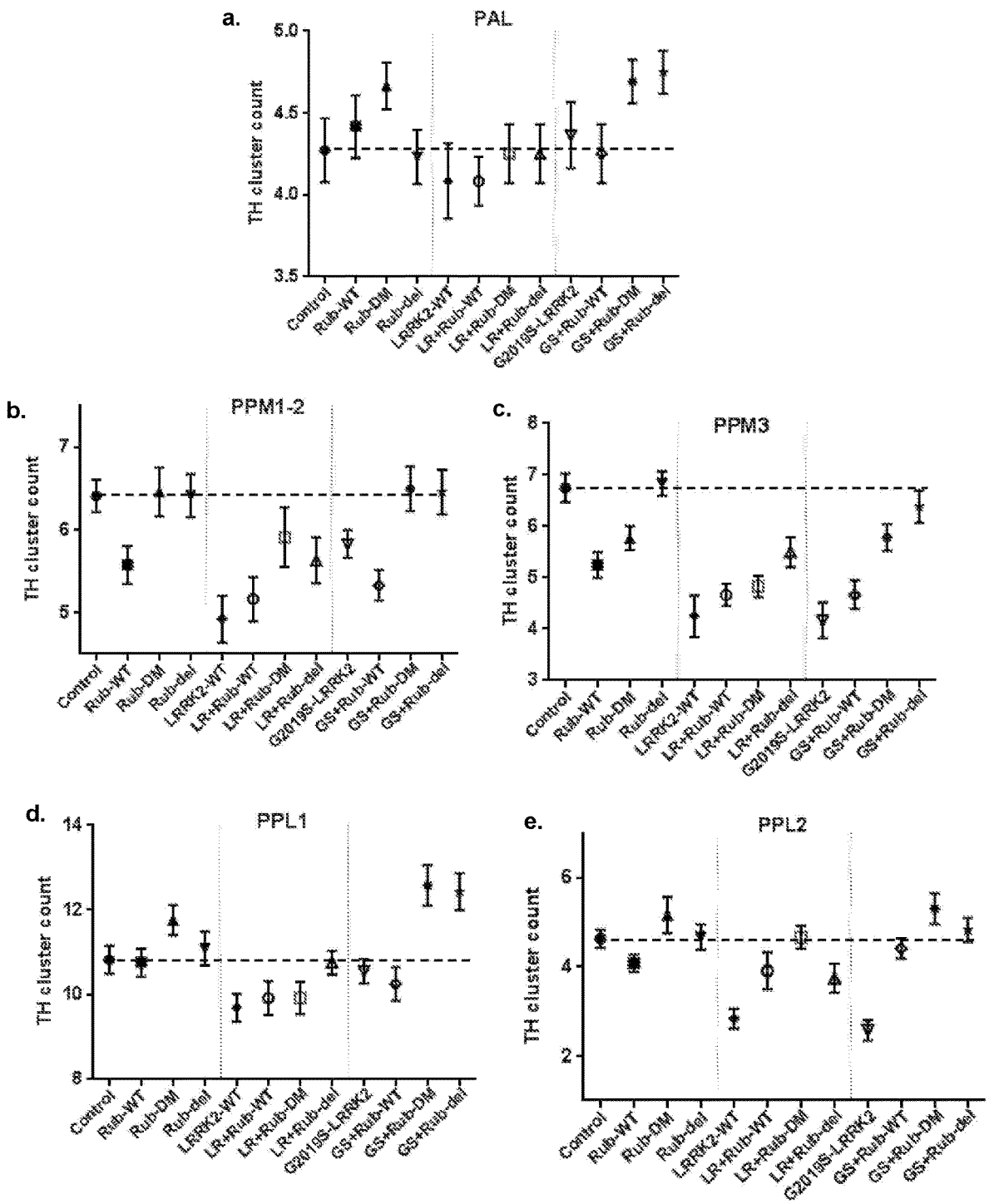

The in vivo effect of LRRK2 and Rubicon was consequently studied by co-expressing human LRRK2 and Rubicon in drosophila. Rubicon mutant lines based on previously identified phosphosites were generated: T166A, S189A, T166A+S189A drosophila Rubicon mutant (DM) and deletion 117-189 (del). T166A yielded no transformants after attempting three insertion sites on two chromosomes and S189A yielded transformants but lacked protein expression when verified by western blotting. As a result, all subsequent studies were carried out with WT, DM and del Rubicon lines after confirmed protein expression. Comparable to the human condition, the drosophila dopaminergic (DA) system is also involved in locomotor control. As distinct clusters of DA neurons identified by positive tyrosine hydroxylase (TH) staining are detectable in the adult fly brain, drosophila viability was assessed based on climbing ability, lifespan and TH-positive expression. First, the co-expression of Rubicon mutants significantly improved the ability of WT-LRRK2 and LRRK2-G2019S drosophila climbing until Day 50. After which, there was a sharp decline in performance that is characteristic of the drosophila model (FIG. 4, Table 2). Next, the co-expression of Rubicon mutants significantly extended the lifespan of WT-LRRK2 drosophila by >25% and the co-expression of Rubicon significantly extended the lifespan of LRRK2-G2019S drosophila by >35% (FIG. 4, Tables 3). Finally, five regions of the aged fly brains were stained for TH-positive neuronal clusters and counted (FIG. 5). The co-expression of Rubicon mutants significantly increased TH count in >2 regions in WT-LRRK2 drosophila and in >3 regions in LRRK2-G2019S drosophila (Table 4).

Drosophila climbing assay statistical analysis in Table 2 was carried out using multiple comparison with Tukey post-hoc test. Statistical significance is achieved when $p < 0.05$ (bold values).

TABLE 2a

LRRK2-WT climbing assay statistical analysis

| DAY | | Control | LR-WT | LWT + RWT | LWT + RDM |
|---|---|---|---|---|---|
| 30 | Control | — | — | — | — |
| 30 | LR-WT | 0.0005 | — | — | — |
| 30 | LWT + RWT | 0.0360 | 0.3559 | — | — |
| 30 | LWT + RDM | 0.9950 | 0.0002 | 0.0154 | — |
| 30 | LWT + Rdel | 0.9688 | 0.0009 | 0.0319 | 0.9977 |
| 40 | Control | — | — | — | — |
| 40 | LR-WT | <.0001 | — | — | — |
| 40 | LWT + RWT | <.0001 | 0.9736 | — | — |
| 40 | LWT + RDM | 0.0820 | <.0001 | <.0001 | — |
| 40 | LWT + Rdel | 0.0003 | 0.0339 | 0.0935 | 0.0500 |
| 50 | Control | — | — | — | — |
| 50 | LR-WT | <.0001 | — | — | — |
| 50 | LWT + RWT | <.0001 | 0.0739 | — | — |
| 50 | LWT + RDM | 0.0195 | <.0001 | <.0001 | — |
| 50 | LWT + Rdel | <.0001 | 0.0227 | 0.0001 | <.0001 |
| 60 | Control | — | — | — | — |
| 60 | LR-WT | <.0001 | — | — | — |
| 60 | LWT + RWT | <.0001 | 0.0061 | — | — |
| 60 | LWT + RDM | <.0001 | 0.9728 | 0.0241 | — |
| 60 | LWT + Rdel | 0.0022 | 0.1005 | <.0001 | 0.0364 |

TABLE 2b

G2019S climbing assay statistical analysis

| Day | | Control | G20195 | GS + RWT | GS + RDM |
|---|---|---|---|---|---|
| 30 | Control | — | — | — | — |
| 30 | G2019S | 0.0016 | — | — | — |
| 30 | GS + RWT | <.0001 | 0.3543 | — | — |
| 30 | GS + RDM | 0.5960 | 0.0517 | 0.0006 | — |
| 30 | GS + Rdel | 0.9694 | 0.0003 | <.0001 | 0.2568 |
| 40 | Control | — | — | — | — |
| 40 | G2019S | <.0001 | — | — | — |
| 40 | GS + RWT | <.0001 | 0.9897 | — | — |
| 40 | GS + RDM | 0.0023 | <.0001 | <.0001 | — |
| 40 | GS + Rdel | 0.0027 | <.0001 | <.0001 | 1.0000 |
| 50 | Control | — | — | — | — |
| 50 | G2019S | <.0001 | — | — | — |
| 50 | GS + RWT | <.0001 | 0.3031 | — | — |
| 50 | GS + RDM | <.0001 | <.0001 | <.0001 | — |
| 50 | GS + Rdel | <.0001 | <.0001 | <.0001 | 0.9860 |
| 60 | Control | — | — | — | — |
| 60 | G2019S | 0.0001 | — | — | — |
| 60 | GS + RWT | 0.0116 | 0.3811 | — | — |
| 60 | GS + RDM | <.0001 | 0.9998 | 0.3015 | — |
| 60 | GS + Rdel | 0.0176 | 0.2933 | 0.9998 | 0.2265 |

Drosophila lifespan statistical analysis was carried out using multiple comparison with Tukey-Kramer method. Statistical significance is achieved when $p < 0.05$ (bold values).

TABLE 3a

LRRK2-WT Lifespan statistical analysis

| Stratum1 | Stratum2 | Tukey |
|---|---|---|
| CTRL | LR-WT | <.0001 |
| CTRL | LR-WTXR-DM | <.0001 |
| CTRL | LR-WTXR-Del | 0.0015 |
| CTRL | LR-WTXR-WT | <.0001 |
| LR-WT | LR-WTXR-DM | 0.0364 |
| LR-WT | LR-WTXR-Del | <.0001 |
| LR-WT | LR-WTXR-WT | 1.0000 |
| LR-WTXR-DM | LR-WTXR-Del | 0.0548 |
| LR-WTXR-DM | LR-WTXR-WT | 0.0497 |
| LR-WTXR-Del | LR-WTXR-WT | <.0001 |

TABLE 3b

G2019S Lifespan statistical analysis

| Stratum1 | Stratum2 | Tukey |
|---|---|---|
| CTRL | G2019S | <.0001 |
| CTRL | G2019S X RDM | 0.0721 |
| CTRL | G2019S X Rdel | <.0001 |
| CTRL | G2019S X RWT | <.0001 |
| G2019S | G2019S X RDM | <.0001 |
| G2019S | G2019S X Rdel | 0.0279 |
| G2019S | G2019S X RWT | 0.0036 |
| G2019S X RDM | G2019S X Rdel | 0.0004 |
| G2019S X RDM | G2019S X RWT | 0.0037 |
| G2019S X Rdel | G2019S X RWT | 0.9802 |

TABLE 4

Statistical significance of Drosophila tyrosine hydroxylase (TH) neuronal staining in aged transgenic flies. Aged (Day 60) transgenic fly brains were stained for TH neuronal clusters in five regions (PPL1, PPL2, PPM1/2, PPM3, PAL) and counted. Statistical significance was analysed using the Student's T-test after adjusting for multiple comparisons.

| | Control | LR-WT | LWT + RWT | LWT + RDM |
|---|---|---|---|---|
| Control | — | — | — | — |
| LR-WT | PPL1, PPL2, PPM3, PPM1/2 | — | — | — |
| LWT + RWT | PPL2, PPM3, PPM1/2 | *PPL1* | — | — |
| LWT + RDM | PPM3 | *PPL2, PPM3, PPM1/2* | *PPL2, PPM1/2* | — |
| LWT + Rdel | PPL2, PPM3, PPM1/2 | *PPL1, PPM3* | — | *PPL1*, PPL2, PPM1/2 |

| | Control | G2019S | GS + RWT | GS + RDM |
|---|---|---|---|---|
| Control | — | — | — | — |
| G2019S | PPL2, PPM3, PPM1/2 | — | — | — |
| GS + RWT | PPM3, PPM1/2 | *PPL2* | — | — |
| GS + RDM | *PPL2* | *PPL2, PPM3, PPM1/2* | *PPL1, PPL2, PPM3* | — |
| GS + Rdel | *PPL1, PPL2* | *PAL, PPL1, PPL2, PPM3, PPM1/2* | *PAL, PPL1, PPL2, PPM3, PPM1/2* | — |

Unpaired T-test

Statistically significant decrease

*Statistically significant increase*

After demonstrating that Rubicon T166 and S189 phosphor-null mutant is able to rescue LRRK2-induced toxicity in vivo, the significance of pT166 Rubicon in human PD samples using the customised pT166 Rubicon sandwich ELISA described herein was next investigated. Firstly, human serum from a local PD cohort harbouring Asian LRRK2 mutations was analysed. PD patient serum, regardless of wild-type or mutant LRRK2, had significantly higher pT166 Rubicon expression compared to healthy controls (FIG. 7 and Table 5). Next, the expression of pT166 Rubicon was examined in macrophages using the customised pT166 Rubicon sandwich ELISA. Firstly, both LRRK2 and Rubicon had comparable endogenous expression in neurons and microglia, which are akin to brain macrophages (FIG. 8a). Mouse macrophages with endogenous LRRK2 knocked out were analysed for pT166 Rubicon expression (FIG. 8b, Table 6). Macrophages lacking LRRK2 had a 30% decrease in endogenous pT166 Rubicon and a 60% decrease in over-expressed pT166 Rubicon.

Figure 9:
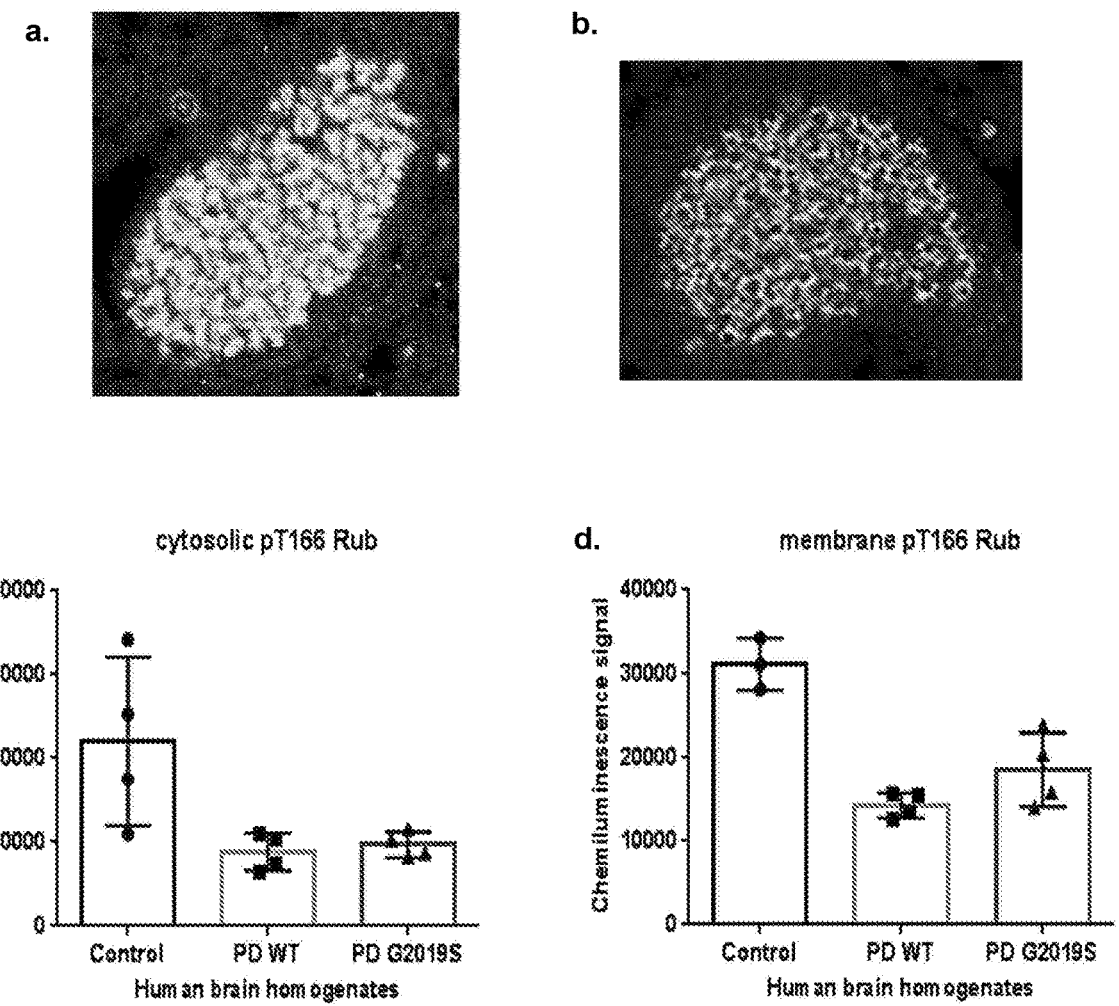

Post-mortem human brain samples were fractionated into soluble and membrane-associated protein fractions and subsequently analysed for pT166 Rubicon expression. Post-mortem human brain sections stained for LRRK2 and Rubicon showed that PD brain had an overall lower expression compared to control brain (FIG. 9). PD brains had significantly decreased pT166 Rubicon expression compared to controls in both the cytosolic and membrane-associated fractions (Table 7). Though differences exist between the peripheral and central nervous system samples examined i.e. serum vs brain, both systems had significantly altered pT166 Rubicon expression.

TABLE 5

Statistical significance of Human serum from a Singapore PD cohort harbouring LRRK2 variant mutations was analysed by pT166 Rubicon sandwich ELISA. Statistical significance was analysed using the Mann-Whitney test. Whole table statistical analysis using 1 way-ANOVA (Kruskal-Wallis test):
$P = 0.0168$

| Mann-Whitney Test | Control- LR WT | Control - LR mutants | PD - LR WT | PD - LR mutants |
|---|---|---|---|---|
| Control - LR WT | — | 0.0.917 | 0.0433 | 0.0172 |
| Control - LR mutants | — | — | 0.0717 | 0.0127 |
| PD - LR WT | — | — | — | — |
| PD - LR mutants | — | — | 0.4285 | — |

TABLE 6

Statistical analysis of LRRK2 macrophage ELISA.

| | Over-expressed Rubicon | Endogenous Rubicon |
|---|---|---|
| Multiple T-test | $P = 0.0154$ | $P = 0.0227$ |

TABLE 7

Statistical significance of Human brain samples from post-mortem Human brains samples were analysed by pT166 Rubicon sandwich ELISA. Statistical significance was analysed using one-way ANOVA and statistical significance is achieved when $P < 0.05$.

| | Cytosolic pT166 Rubicon | Membrane pT166 Rubicon |
|---|---|---|
| One-way ANOVA | $P = 0.022$ | $P = 0.0004$ |

The altered expression of pT166 Rubicon in PD serum and post-mortem PD brain compared to healthy controls displayed its potential as a PD diagnostic biomarker.

In vivo, the co-expression of Rubicon phosphor-null mutants was able to rescue LRRK2-induced toxicity. This suggests that Rubicon phosphosites, T166 and S189, are possible drug target sites for LRRK2-linked diseases. Many drugs have off-target effects, therefore an allosteric inhibitor to LRRK2-specific substrate sites will enhance precision and minimise adverse off-target effects.

An antibody was formed using the synthesized peptide DAHV{pThr}AMLQCLEAVE (SEQ ID NO. 2) conjugated to Keyhole limpet hemocyanin (KLH) and the resultant immunogen peptide was used to generate phosphor-specific antibody in a mammal.

Few bona fide LRRK2 substrates have been identified to date. Among them, not many were methodically screened for LRRK2-specific phosphosites.

Polyclonal antibodies were developed in 3 Balb/c mice and 3 C57 mice using the synthesized peptide DAHV{pThr}AMLQCLEAVE (SEQ ID NO. 2) conjugated to Keyhole limpet hemocyanin (KLH). Test bleeds were taken after the $3^{rd}$ and $5^{th}$ immunisation with the peptide conjugate. To test titer and specificity of the antibodies 98 well plates were coated with either SEQ ID NO. 2: DAHV{pThr}AMLQCLEAVE or SEQ ID NO. 14: DAHVTAMLQCLEAVE epitopes, whereby the sequence surrounding T166 of the Rubicon protein of SEQ ID NO. 1 was either phosphorylated or not phosphorylated. Samples of pre-immunised serum and antiserum collected after the $3^{rd}$ and $5^{th}$ immunisation were then used in an indirect ELISA assay in phosphate buffered saline, pH 7.4 to detect the phosphorylated antigen SEQ ID NO. 2 or the un-phosphorylated antigen SEQ ID NO. 14 across a series of supernatant dilutions. The secondary antibody was a per-oxidase-AffiniPure Goat Anti-Mouse IgG, Fcγ Fragment Specific (min X Hu, Boy Hrs Sr Prot). The results are listed in table 8. The dilution extended to 1:512,000, however the results for the full range of dilution is not listed.

TABLE 8

ELISA results for polyclonal antibodies.

| Serum type | sample | Supernatant dilution | | | | | | Blank | | SEQ ID NO. |
|---|---|---|---|---|---|---|---|---|---|---|
| | | 1:1,000 | 1:2,000 | 1:4,000 | 1:8,000 | 1:16,000 | 1:32,0000 | PBS | Titer | coating |
| Pre-immunisation | 1 | 0.08 | — | — | — | — | — | 0.06 | <1,000 | 2 |
| | | 0.09 | — | — | — | — | — | 0.08 | <1,000 | 14 |

TABLE 8-continued

ELISA results for polyclonal antibodies.

| Serum type | sample | Supernatant dilution | | | | | | Blank PBS | Titer | SEQ ID NO. coating |
|---|---|---|---|---|---|---|---|---|---|---|
| | | 1:1,000 | 1:2,000 | 1:4,000 | 1:8,000 | 1:16,000 | 1:32,0000 | | | |
| serum | 2 | 0.07 | — | — | — | — | — | 0.06 | <1,000 | 2 |
| | | 0.06 | — | — | — | — | — | 0.08 | <1,000 | 14 |
| antiserum collected after the 3rd immunisation | 1 | 1.62 | 0.96 | 0.62 | 0.40 | 0.25 | 0.16 | 0.06 | 32,000 | 2 |
| | | 0.09 | 0.08 | 0.07 | 0.07 | 0.06 | 0.06 | 0.08 | <1,000 | 14 |
| | 2 | 2.31 | 1.27 | 0.74 | 0.45 | 0.31 | 0.19 | 0.06 | 64,000 | 2 |
| | | 0.1 | 0.8 | 0.08 | 0.06 | 0.07 | 0.06 | 0.08 | <1,000 | 14 |
| antiserum collected after the 4rd immunisation | 1 | 2.62 | 2.06 | 1.84 | 1.29 | 0.81 | 0.44 | 0.06 | 512,000 | 2 |
| | | 1.13 | 0.71 | 0.35 | 0.21 | 0.14 | 0.10 | 0.08 | 16,000 | 14 |
| | 2 | 2.64 | 2.17 | 1.78 | 1.19 | 0.75 | 0.42 | 0.06 | 512,000 | 2 |
| | | 1.72 | 1.15 | 0.77 | 0.50 | 0.34 | 0.19 | 0.08 | 64,000 | 14 |
| antiserum collected after the 5rd immunisation | 1 | 2.89 | 2.60 | 1.98 | 1.88 | 1.07 | 0.71 | 0.06 | 64,000 | 2 |
| | | 1.99 | 1.57 | 1.00 | 0.75 | 0.42 | 0.25 | 0.08 | 16,000 | 14 |
| | 2 | 2.59 | 2.41 | 1.88 | 1.41 | 0.96 | 0.51 | 0.06 | 64,000 | 2 |
| | | 2.00 | 1.77 | 1.00 | 0.94 | 0.57 | 0.51 | 0.08 | 64,000 | 14 |

Monoclonal antibodies were developed against the target site and 5 primary clones were selected with 2 monoclonal cell lines being established for each clone. To test titer and specificity of the antibodies 98 well plates were coated with either SEQ ID NO. 2: DAHV{pThr}AMLQCLEAVE or SEQ ID NO. 14: DAHVTAMLQCLEAVE epitopes, whereby the sequence surrounding T166 of the Rubicon protein of SEQ ID NO. 1 was either phosphorylated or not phosphorylated. All of the 10 antibody cell lines were then used in an indirect ELISA assay in phosphate buffered saline, pH 7.4 to detect the phosphorylated antigen SEQ ID NO. 2 or the un-phosphorylated antigen SEQ ID NO. 14 across a series of supernatant dilutions. The secondary antibody was a peroxidase-AffiniPure Goat Anti-Mouse IgG, Fcγ Fragment Specific (min X Hu, Boy Hrs Sr Prot). The results are listed in table 9.

TABLE 9

ELISA results of hybridoma culture supernatant

| Primary clone No. | Cell lines | Supernatant dilution | | | | | | Blank PBS | Titer | SEQ ID NO. coating | isotype |
|---|---|---|---|---|---|---|---|---|---|---|---|
| | | 1:10 | 1:30 | 1:90 | 1:270 | 1:810 | 1:2,430 | | | | |
| 1 | 4B9-1 | 2.60 | 2.56 | 2.54 | 2.33 | 1.83 | 0.98 | 0.08 | >2,430 | 2 | IgG2a,K |
| | | 0.07 | 0.07 | 0.07 | 0.06 | 0.06 | 0.06 | 0.08 | <10 | 14 | |
| | 4B9-2 | 2.57 | 2.55 | 2.36 | 2.11 | 1.32 | 0.72 | 0.08 | >2,430 | 2 | IgG2a,K |
| | | 0.09 | 0.08 | 0.07 | 0.06 | 0.06 | 0.06 | 0.08 | <10 | 14 | |
| 2 | 6A1-1 | 2.60 | 2.31 | 1.95 | 1.31 | 0.59 | 0.24 | 0.08 | >2,430 | 2 | IgG2a,K |
| | | 0.07 | 0.06 | 0.06 | 0.06 | 0.06 | 0.05 | 0.08 | <10 | 14 | |
| | 6A1-2 | 2.59 | 2.30 | 2.12 | 1.45 | 0.88 | 0.49 | 0.08 | >2,430 | 2 | IgG2a,K |
| | | 0.06 | 0.06 | 0.06 | 0.06 | 0.06 | 0.06 | 0.08 | <10 | 14 | |
| 3 | 9B7-1 | 2.65 | 2.64 | 2.44 | 2.05 | 1.48 | 1.05 | 0.08 | >2,430 | 2 | IgG2,K |
| | | 0.07 | 0.06 | 0.06 | 0.06 | 0.05 | 0.05 | 0.08 | <10 | 14 | |
| | 9B7-2 | 2.75 | 2.63 | 2.59 | 1.99 | 1.32 | 0.80 | 0.08 | >2,430 | 2 | IgG2,K |
| | | 0.07 | 0.07 | 0.07 | 0.06 | 0.06 | 0.06 | 0.08 | <10 | 14 | |
| 4 | 9D1-1 | 2.46 | 2.27 | 2.18 | 2.14 | 1.60 | 1.02 | 0.08 | >2,430 | 2 | IgG2a,K |
| | | 0.09 | 0.07 | 0.07 | 0.07 | 0.06 | 0.06 | 0.08 | <10 | 14 | |
| | 9D1-2 | 2.51 | 2.46 | 2.42 | 2.36 | 1.93 | 1.36 | 0.08 | >2,430 | 2 | IgG2a,K |
| | | 0.15 | 0.15 | 0.06 | 0.06 | 0.06 | 0.06 | 0.08 | <10 | 14 | |
| 5 | 12H1-1 | 2.39 | 2.34 | 2.30 | 1.97 | 1.51 | 0.99 | 0.08 | >2,430 | 2 | IgG2a,K |
| | | 0.07 | 0.07 | 0.06 | 0.06 | 0.05 | 0.05 | 0.08 | <10 | 14 | |
| | 12H2-2 | 2.45 | 2.43 | 2.38 | 2.12 | 1.60 | 0.95 | 0.08 | >2,430 | 2 | IgG2a,K |
| | | 0.08 | 0.07 | 0.07 | 0.06 | 0.05 | 0.05 | 0.08 | <10 | 14 | |

A specific monoclonal antibody against the identified target site was customised and a sandwich ELISA using the customised pT166 Rubicon antibody was developed. The pT166 Rubicon sandwich ELISA was validated with human PD serum and brain samples. The developed pT166 Rubicon sandwich ELISA may be used as a diagnostic assay for PD.

The produced monoclonal antibody was sequenced. Total RNA was isolated from the hybridoma cells following the technical manual of TRIzol® Reagent. Total RNA was then reverse-transcribed into cDNA using either isotype-specific anti-sense primers or universal primers following the technical manual of PrimeScript™ 1st Strand cDNA Synthesis Kit. Antibody fragments of heavy chain and light chain were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. The consensus sequence is provided below. All 5 clones screened had at least 99% amino acid sequence identity. Similarly, analysis found at least 96% sequence identity in both the heavy chain (96.53% nucleotide identity) and the light chain (98.64% nucleotide identity).

Heavy chain: cDNA sequence (420 bp)
Signal sequence-*FR1*-CDR1-*FR2*-CDR2-*FR3*-CDR3-*FR4*, SEQ ID NO. 10:
ATGAACTTAGGGCTCAGCTTCATTTTCCTTGCCCTTATTTTAAAAGGTGTCCAGTGTG*AG*

*GTGCAGCTGGTGGAGTCTGGGGGAGGCTTAGTGCAGCCTGGAGGGTCCCTGAAACTC*

*TCCTGTGCAGCCTCTGGATTCACTTTCACT*AATTATGGCGTGTCT*TGGGTTCGCCAGAC*

*TCCAGACAAGAGGCTGGAGTTGGTCGCA*ACCATTAATAGTAATGGTGGTAGTAAATAT

TATCCAGACAGTGTGAAGGGC*CGATTCACCATTTCCAGAGACACTGCCAAGAACACCC*

*TGTACCTGCATATGAGCAGTCTGAAGTCTGAGGACACAGCCATGTATTACTGTGCAAGA*

GATGTATGGTTACGACGTCAGTGGTACTTCGATGTC*TGGGGCGCAGGGACCACGGTC*

*ACCGTCTCCTCA*.

Light chain: DNA sequence (393 bp)
Signal sequence-*FR1*-CDR1-*FR2*-CDR2-*FR3*-CDR3-*FR4*, SEQ ID NO. 11:
ATGAAGTTGCCTGTTAGGCTGTTGGTGCTGATGTTCTGGATTCCTGCTTCCAGCAGTGA

TGTTGTGATGACCCAAACTCCTCTCTCCCTGCCTGTCAGTCTTGGAGATCCAGCCTCCA

TCTCTTGCAGATCTAGTCAGAGCCTTGTACACAGTAATGGAAACACCTATTTACAT*TG*

*GTACCTGCAGAAGACAGGCCAGTCTCCAAAGCTCCTGATCTAC*AAACTTTCCAACCGA

TTTTCT*GGGGTCCCAGACAGGTTCAGTGGCAGTGGATCAGGGACAGATTTCACACTCA*

*AGATCAGCAGAGTGGAGGCTGAGGATCTGGGAGTTTATTTCTGC*TCTCAAAGTACACA

TGTTCCTCTCACG*TTCGGTGCTGGGACCAAGCTGGAGCTGAAA*.

Light chain: Amino acid sequence (131 aa)
Signal peptide-*FR1*-CDR1-*FR2*-CDR2-*FR3*-CDR3-*FR4*, SEQ ID NO. 12:
MKLPVRLLVLMFWIPASSS*DVVMTQTPLSLPVSLGDPASISC*RSSQSLVHSNGNTYLH*WYL*

*QKTGQSPKLLIY*KLSNRFS*GVPDRFSGSGSGTDFTLKISRVEAEDLGVYFC*SQSTHVPLT*F*

*GAGTKLELK*.

Heavy chain: Amino acid sequence (140 aa)
Signal peptide-*FR1*-CDR1-*FR2*-CDR2-*FR3*-CDR3-*FR4*, SEQ ID NO. 13:
MNLGLSFIFLALILKGVQC*EVQLVESGGGLVQPGGSLKLSCAASGFTFT*NYGVS*WVRQTPD*

*KRLELVA*TINSNGGSKYYPDSVKG*RFTISRDTAKNTLYLHMSSLKSEDTAMYYCAR***DVWLR*

RQWYFDV*WGAGTTVTVSS*.

Identified LRRK2-specific Rubicon phosphosites, T166 and s189, LRRK2-linked toxicity was able to be rescued in vivo, highlighting the phosphosites potential as drug target sites.

Current work aims to build on pT166 Rubicon as a diagnostic biomarker for PD. This is achieved by assaying a small amount of patient serum protein (2 µg) with the developed pT166 Rubicon sandwich ELISA.

The quantified pT166 Rubicon expression in patient serum will determine if the assayed sample belongs to healthy control or PD group based on pre-set thresholds. Ideally, if pT166 Rubicon expression varies between short disease duration (<5 years) and long disease duration (>5 years), the quantified pT166 Rubicon expression will be able to reveal if PD is early stage or late stage.

In various embodiments Rubicon is an amino acid sequence represented by SEQ ID NO.1:

MRPEGAGMELGGGEERLPEESRREHWQLLGNLKTTVEGLVSTNSPNVWS

KYGGLERLCRDMQSILYHGLIRDQACRRQTDYWQFVKDIRWLSPHSALH

VEKFISVHENDQSSADGASERAVAELWLQHSLQYHCLSAQLRPLLGDRQ

-continued
YIRKFYTDAAFLLSDAHVTAMLQCLEAVEQNNPRLLAQIDASMFARKHE

SPLLVTKSQSLTALPSSTYTPPNSYAQHSYFGSFSSLHQSVPNNGSERR

STSFPLSGPPRKPQESRGHVSPAEDQTIQAPPVSVSALARDSPLTPNEM

SSSTLTSPIEASWVSSQNDSPGDASEGPEYLAIGNLDPRGRTASCQSHS

SNAESSSSNLFSSSSSQKPDSAASSLGDQEGGGESQLSSVLRRSSFSEG

QTLTVTSGAKKSHIRSHSDTSIASRGAPESCNDKAKLRGPLPYSGQSSE

VSTPSSLYMEYEGGRYLCSGEGMFRRPSEGQSLISYLSEQDFGSCADLE

KENAHFSISESLIAAIELMKCNMMSQCLEEEEVEEEDSDREIQELKQKI

RLRRQQIRTKNLLPMYQEAEHGSFRVTSSSSQFSSRDSAQLSDSGSADE

VDEFEIQDADIRRNTASSSKSFVSSQSFSHCFLHSTSAEAVAMGLLKQF

EGMQLPAASELEWLVPEHDAPQKLLPIPDSLPISPDDGQHADIYKLRIR

VRGNLEWAPPRPQIIFNVHPAPTRKIAVAKQNYRCAGCGIRTDPDYIKR

LRYCEYLGKYFCQCCHENAQMAIPSRVLRKWDFSKYYVSNFSKDLLIKI

WNDPLFNVQDINSALYRKVKLLNQVRLLRVQLCHMKNMFKTCRLAKELL

-continued

```
DSFDTVPGHLTEDLHLYSLNDLTATRKGELGPRLAELTRAGATHVERCM

LCQAKGFICEFCQNEDDIIFPFELHKCRTCEECKACYHKACFKSGSCPR

CERLQARREALARQSLESYLSDYEEEPAEALALEAAVLEAT
```

Whereby the phosphosites T166 and S189 are represented as the bold underlined amino acids.

```
SEQ ID NO. 2:
DAHV{pThr}AMLQCLEAVE.

SEQ ID NO. 3:
MASGSCQGCEEDEETLKKLIVRLNNVQEGKQIETLVQILEDLLVFTYSE

RASKLFQGKNIHVPLLIVLDSYMRVASVQQVGWSLLCKLIEVCPGTMQS

LMGPQDVGNDWEVLGVHQLILKMLTVHNASVNLSVIGLKTLDLLLTSGK

ITLLILDEESDIFMLIFDAMHSFPANDEVQKLGCKALHVLFERVSEEQL

TEFVENKDYMILLSALTNFKDEEEIVLHVLHCLHSLAIPCNNVEVLMSG

NVRCYNIVVEAMKAFPMSERIQEVSCCLLHRLTLGNFFNILVLNEVHEF

VVKAVQQYPENAALQISALSCLALLTETIFLNQDLEEKNENQENDDEGE

EDKLFWLEACYKALTWHRKNKHVQEAACWALNNLLMYQNSLHEKIGDED

GHFPAHREVMLSMLMHSSSKEVFQASANALSTLLEQNVNFRKILLSKGI

HLNVLELMQKHIHSPEVAESGCKMLNHLFEGSNTSLDIMAAVVPKILTV

MKRHETSLPVQLEALRAILHFIVPGMPEESREDTEFHHKLNMVKKQCFK

NDIHKLVLAALNRFIGNPGIQKCGLKVISSIVHFPDALEMLSLEGAMDS

VLHTLQMYPDDQEIQCLGLSLIGYLITKKNVFIGIGHLLAKILVSSLYR

FKDVAEIQTKGFQTILAILKLSASFSKLLVHHSFDLVIFHQMSSNIMEQ

KDQQFLNLCCKCFAKVAMDDYLKNVMLERACDQNNSIMVECLLLLGADA

NQAKEGSSLICQVCEKESSPKLVELLLNSGSREQDVRKALTISIGKGDS

QIISLLLRRLALDVANNSICLGGFCIGKVEPSWLGPLFPDKTSNLRKQT

NIASTLARMVIRYQMKSAVEEGTASGSDGNFSEDVLSKFDEWTFIPDSS

MDSVFAQSDDLDSEGSEGSFLVKKKSNSISVGEFYRDAVLQRCSPNLQR

HSNSLGPIFDHEDLLKRKRKILSSDDSLRSSKLQSHMRHSDSISSLASE

REYITSLDLSANELRDIDALSQKCCISVHLEHLEKLELHQNALTSFPQQ

LCETLKSLTHLDLHSNKFTSFPSYLLKMSCIANLDVSRNDIGPSVVLDP

TVKCPTLKQFNLSYNQLSFVPENLTDVVEKLEQLILEGNKISGICSPLR

LKELKILNLSKNHISSLSENFLEACPKVESFSARMNFLAAMPFLPPSMT

ILKLSQNKFSCIPEAILNLPHLRSLDMSSNDIQYLPGPAHWKSLNLREL

LFSHNQISILDLSEKAYLWSRVEKLHLSHNKLKEIPPEIGCLENLTSLD

VSYNLELRSFPNEMGKLSKIWDLPLDELHLNFDFKHIGCKAKDIIRFLQ

QRLKKAVPYNRMKLMIVGNTGSGKTTLLQQLMKTKKSDLGMQSATVGID

VKDWPIQIRDKRKRDLVLNVWDFAGREEFYSTHPHFMTQRALYLAVYDL

SKGQAEVDAMKPWLFNIKARASSSPVILVGTHLDVSDEKQRKACMSKIT

KELLNKRGFPAIRDYHFVNATEESDALAKLRKTIINESLNFKIRDQLVV

GQLIPDCYVELEKIILSERKNVPIEFPVIDRKRLLQLVRENQLQLDENE

LPHAVHFLNESGVLLHFQDPALQLSDLYFVEPKWLCKIMAQILTVKVEG

CPKHPKGIISRRDVEKFLSKKRKFPKNYMSQYFKLLEKFQIALPIGEEY

LLVPSSLSDHRPVIELPHCENSEIIIRLYEMPYFPMGFWSRLINRLLEI

SPYMLSGRERALRPNRMYWRQGIYLNWSPEAYCLVGSEVLDNHPESFLK

ITVPSCRKGCILLGQVVDHIDSLMEEWFPGLLEIDICGEGETLLKKWAL

YSFNDGEEHQKILLDDLMKKAEEGDLLVNPDQPRLTIPISQIAPDLILA

DLPRNIMLNNDELEFEQAPEFLLGDGSFGSVYRAAYEGEEVAVKIFNKH

TSLRLLRQELVVLCHLHHPSLISLLAAGIRPRMLVMELASKGSLDRLLQ

QDKASLTRTLQHRIALHVADGLRYLHSAMIIYRDLKPHNVLLFTLYPNA

AIIAKIADYGIAQYCCRMGIKTSEGTPGFRAPEVARGNVIYNQQADVYS

FGLLLYDILTTGGRIVEGLKFPNEFDELEIQGKLPDPVKEYGCAPWPMV

EKLIKQCLKENPQERPTSAQVFDILNSAELVCLTRRILLPKNVIVECMV

ATHHNSRNASIWLGCGHTDRGQLSFLDLNTEGYTSEEVADSRILCLALV

HLPVEKESWIVSGTQSGTLLVINTEDGKKRHTLEKMTDSVTCLYCNSFS

KQSKQKNFLLVGTADGKLAIFEDKTVKLKGAAPLKILNIGNVSTPLMCL

SESTNSTERNVMWGGCGTKIFSFSNDFTIQKLIETRTSQLFSYAAFSDS

NIITVVVDTALYIAKQNSPVVEVWDKKTEKLCGLIDCVHFLREVMVKEN

KESKHKMSYSGRVKTLCLQKNTALWIGTGGGHILLLDLSTRRLIRVIYN

FCNSVRVMMTAQLGSLKNVMLVLGYNRKNTEGTQKQKEIQSCLTVWDIN

LPHEVQNLEKHIEVRKELAEKMRRTSVE
```

It should be further appreciated by the person skilled in the art that variations and combinations of features described above, not being alternatives or substitutes, may be combined to form yet further embodiments falling within the intended scope of the invention.

As would be understood by a person skilled in the art, each embodiment, may be used in combination with other embodiment or several embodiments.

The invention claimed is:

1. An in vitro method of detecting phosphorylation of a Rubicon protein comprising:

isolating proteins from a sample;

contacting the isolated proteins with an antibody that binds to a phosphorylated Threonine at 166 of a Rubicon protein to form a complex, the antibody comprising amino acid sequences:

i) LC-CDR1:
(SEQ ID NO. 4)
RSSQSLVHSNGNTYLH;

ii) LC-CDR2:
(SEQ ID NO. 5)
KLSNRFS;

iii) LC-CDR3:
(SEQ ID NO. 6)
SQSTHVPLT;

iv) HC-CDR1:
(SEQ ID NO. 7)
NYGVS;

v) HC-CDR2:
(SEQ ID NO. 8)
TINSNGGSKYYPDSVKG; and vi) HC-CDR3:
(SEQ ID NO. 9)
DVWLRRQWYFDV;

detecting the complex wherein detection of the complex that varies from a predetermined value indicates that the sample comes from a subject having a disease associated with Leucine-rich repeat kinase 2 (LRRK2).

2. The in vitro method according to claim 1, wherein the disease associated with Leucine-rich repeat kinase 2 (LRRK2) is Parkinson's disease.

3. The in vitro method according to claim 1, wherein the antibody is a chimeric humanised antibody.

4. The in vitro method according to claim 1, wherein the antibody is a monoclonal antibody.

5. The in vitro method according to claim 1, wherein the complex is detected with an enzyme linked immunosorbent assay.

6. The in vitro method according to claim 1, wherein the subject having a disease associated with Leucine-rich repeat kinase 2 (LRRK2) is treated with a compound able to block interaction of LRRK2 with Threonine 166 of the Rubicon protein, the compound comprising a treatment antibody that binds to phosphorylated Threonine at 166 of the Rubicon protein, the treatment antibody comprising amino acid sequences.

```
i) LC-CDR1:
                                 (SEQ ID NO. 4)
RSSQSLVHSNGNTYLH;

ii) LC-CDR2:
                                 (SEQ ID NO. 5)
KLSNRFS;

iii) LC-CDR3:
                                 (SEQ ID NO. 6)
SQSTHVPLT;

iv) HC-CDR1:
                                 (SEQ ID NO. 7)
NYGVS;

v) HC-CDR2:
                                 (SEQ ID NO. 8)
TINSNGGSKYYPDSVKG; and vi) HC-CDR3:
                                 (SEQ ID NO. 9)
DVWLRRQWYFDV.
```

7. The in vitro method according to claim 6, wherein the treatment antibody is a chimeric humanised antibody.

8. The in vitro method according to claim 6, wherein the treatment antibody is a monoclonal antibody.

9. An antibody that binds to phosphorylated Threonine at 166 of a Rubicon protein, the antibody comprising amino acid sequences:

```
i) LC-CDR1:
                                 (SEQ ID NO. 4)
RSSQSLVHSNGNTYLH;

ii) LC-CDR2:
                                 (SEQ ID NO. 5)
KLSNRFS;

iii) LC-CDR3:
                                 (SEQ ID NO. 6)
SQSTHVPLT;

iv) HC-CDR1:
                                 (SEQ ID NO. 7)
NYGVS;

v) HC-CDR2:
                                 (SEQ ID NO. 8)
TINSNGGSKYYPDSVKG; and vi) HC-CDR3:
                                 (SEQ ID NO. 9)
DVWLRRQWYFDV.
```

10. The antibody according to claim 9, wherein the antibody is a chimeric humanised antibody.

11. The antibody according to claim 9, wherein the antibody is a monoclonal antibody.

12. An inhibitor of Rubicon interaction with Leucine-rich repeat kinase 2 (LRRK2) comprising a compound able to block interaction of LRRK2 with Threonine 166 of the Rubicon protein, the compound comprising an antibody that binds to phosphorylated Threonine at 166 of the Rubicon protein, the antibody comprising amino acid sequences:

```
i) LC-CDR1:
                                 (SEQ ID NO. 4)
RSSQSLVHSNGNTYLH;

ii) LC-CDR2:
                                 (SEQ ID NO. 5)
KLSNRFS;

iii) LC-CDR3:
                                 (SEQ ID NO. 6)
SQSTHVPLT;

iv) HC-CDR1:
                                 (SEQ ID NO. 7)
NYGVS;

v) HC-CDR2:
                                 (SEQ ID NO. 8)
TINSNGGSKYYPDSVKG; and vi) HC-CDR3:
                                 (SEQ ID NO. 9)
DVWLRRQWYFDV.
``` iv) HC-CDR1: NYGVS (SEQ ID NO. 7);
v) HC-CDR2: TINSNGGSKYYPDSVKG (SEQ ID NO. 8); and
vi) HC-CDR3: DVWLRRQWYFDV (SEQ ID NO. 9).

13. A method of treating a subject in need having a disease associated with Leucine-rich repeat kinase 2 (LRRK2) comprising:
administering a compound able to block interaction of LRRK2 with Threonine 166 of the Rubicon protein, the compound comprising an antibody that binds to phosphorylated Threonine at 166 of the Rubicon protein, the antibody comprising amino acid sequences:

```
i) LC-CDR1:
                                 (SEQ ID NO. 4)
RSSQSLVHSNGNTYLH;

ii) LC-CDR2:
                                 (SEQ ID NO. 5)
KLSNRFS;

iii) LC-CDR3:
                                 (SEQ ID NO. 6)
SQSTHVPLT;

iv) HC-CDR1:
                                 (SEQ ID NO. 7)
NYGVS;

v) HC-CDR2:
                                 (SEQ ID NO. 8)
TINSNGGSKYYPDSVKG; and
```

```
        -continued
vi) HC-CDR3:
                              (SEQ ID NO. 9)
    DVWLRRQWYFDV.
```

14. The method according to claim 13, wherein the antibody is a chimeric humanised antibody.

15. The method according to claim 13, wherein the antibody is a monoclonal antibody.

16. The in vitro method according to claim 1, wherein the antibody comprises a primary antibody and the step of detecting the complex comprises contacting the complex with a secondary antibody that binds to the primary antibody.

17. The in vitro method according to claim 1, wherein the antibody comprises amino acid sequences set forth in SEQ ID NO. 12 and SEQ ID NO. 13; or a functional variant with 99% amino acid sequence identity to SEQ ID NO. 12 or SEQ ID NO. 13.

18. The antibody according to claim 9, comprising amino acid sequences set forth in SEQ ID NO. 12 and SEQ ID NO. 13; or a functional variant with 99% amino acid sequence identity to SEQ ID NO. 12 or SEQ ID NO. 13.

19. The inhibitor according to claim 12, wherein the antibody comprises amino acid sequences set forth in SEQ ID NO. 12 and SEQ ID NO. 13; or a functional variant with 99% amino acid sequence identity to SEQ ID NO. 12 or SEQ ID NO. 13.

20. The method according to claim 13, wherein the antibody comprises amino acid sequences set forth in SEQ ID NO. 12 and SEQ ID NO. 13; or a functional variant with 99% amino acid sequence identity to SEQ ID NO. 12 or SEQ ID NO. 13.

* * * * *

SEQUENCE LISTING

```
<160> NUMBER OF SEQ ID NOS: 14

<210> SEQ ID NO 1
<211> LENGTH: 972
<212> TYPE: PRT
<213> ORGANISM: Homo sapiens
<220> FEATURE:
<221> NAME/KEY: MISC_FEATURE
<222> LOCATION: (166)..(166)
<223> OTHER INFORMATION: Phosphosite
<220> FEATURE:
```

<221> NAME/KEY: MISC_FEATURE
<222> LOCATION: (189)..(189)
<223> OTHER INFORMATION: Phosphosite

<400> SEQUENCE: 1

```
Met Arg Pro Glu Gly Ala Gly Met Glu Leu Gly Gly Gly Glu Arg
1               5                   10                  15

Leu Pro Glu Glu Ser Arg Arg Glu His Trp Gln Leu Leu Gly Asn Leu
                20                  25                  30

Lys Thr Thr Val Glu Gly Leu Val Ser Thr Asn Ser Pro Asn Val Trp
            35                  40                  45

Ser Lys Tyr Gly Gly Leu Glu Arg Leu Cys Arg Asp Met Gln Ser Ile
    50                  55                  60

Leu Tyr His Gly Leu Ile Arg Asp Gln Ala Cys Arg Arg Gln Thr Asp
65                  70                  75                  80

Tyr Trp Gln Phe Val Lys Asp Ile Arg Trp Leu Ser Pro His Ser Ala
                85                  90                  95

Leu His Val Glu Lys Phe Ile Ser Val His Glu Asn Asp Gln Ser Ser
                100                 105                 110

Ala Asp Gly Ala Ser Glu Arg Ala Val Ala Glu Leu Trp Leu Gln His
            115                 120                 125

Ser Leu Gln Tyr His Cys Leu Ser Ala Gln Leu Arg Pro Leu Leu Gly
    130                 135                 140

Asp Arg Gln Tyr Ile Arg Lys Phe Tyr Thr Asp Ala Ala Phe Leu Leu
145                 150                 155                 160

Ser Asp Ala His Val Thr Ala Met Leu Gln Cys Leu Glu Ala Val Glu
                165                 170                 175

Gln Asn Asn Pro Arg Leu Leu Ala Gln Ile Asp Ala Ser Met Phe Ala
                180                 185                 190

Arg Lys His Glu Ser Pro Leu Leu Val Thr Lys Ser Gln Ser Leu Thr
            195                 200                 205

Ala Leu Pro Ser Ser Thr Tyr Thr Pro Pro Asn Ser Tyr Ala Gln His
    210                 215                 220

Ser Tyr Phe Gly Ser Phe Ser Ser Leu His Gln Ser Val Pro Asn Asn
225                 230                 235                 240

Gly Ser Glu Arg Arg Ser Thr Ser Phe Pro Leu Ser Gly Pro Pro Arg
                245                 250                 255

Lys Pro Gln Glu Ser Arg Gly His Val Ser Pro Ala Glu Asp Gln Thr
                260                 265                 270

Ile Gln Ala Pro Pro Val Ser Val Ser Ala Leu Ala Arg Asp Ser Pro
            275                 280                 285

Leu Thr Pro Asn Glu Met Ser Ser Ser Thr Leu Thr Ser Pro Ile Glu
    290                 295                 300

Ala Ser Trp Val Ser Ser Gln Asn Asp Ser Pro Gly Asp Ala Ser Glu
305                 310                 315                 320

Gly Pro Glu Tyr Leu Ala Ile Gly Asn Leu Asp Pro Arg Gly Arg Thr
                325                 330                 335

Ala Ser Cys Gln Ser His Ser Ser Asn Ala Glu Ser Ser Ser Ser Asn
            340                 345                 350

Leu Phe Ser Ser Ser Ser Ser Gln Lys Pro Asp Ser Ala Ala Ser Ser
    355                 360                 365

Leu Gly Asp Gln Glu Gly Gly Glu Ser Gln Leu Ser Ser Val Leu
    370                 375                 380

Arg Arg Ser Ser Phe Ser Glu Gly Gln Thr Leu Thr Val Thr Ser Gly
```

```
            385                 390                 395                 400
Ala Lys Lys Ser His Ile Arg Ser His Ser Asp Thr Ser Ile Ala Ser
                    405                 410                 415

Arg Gly Ala Pro Glu Ser Cys Asn Asp Lys Ala Lys Leu Arg Gly Pro
                420                 425                 430

Leu Pro Tyr Ser Gly Gln Ser Ser Glu Val Ser Thr Pro Ser Ser Leu
            435                 440                 445

Tyr Met Glu Tyr Glu Gly Gly Arg Tyr Leu Cys Ser Gly Glu Gly Met
        450                 455                 460

Phe Arg Arg Pro Ser Glu Gly Gln Ser Leu Ile Ser Tyr Leu Ser Glu
465                 470                 475                 480

Gln Asp Phe Gly Ser Cys Ala Asp Leu Glu Lys Glu Asn Ala His Phe
                485                 490                 495

Ser Ile Ser Glu Ser Leu Ile Ala Ala Ile Glu Leu Met Lys Cys Asn
                500                 505                 510

Met Met Ser Gln Cys Leu Glu Glu Glu Val Glu Glu Glu Asp Ser
        515                 520                 525

Asp Arg Glu Ile Gln Glu Leu Lys Gln Lys Ile Arg Leu Arg Arg Gln
        530                 535                 540

Gln Ile Arg Thr Lys Asn Leu Leu Pro Met Tyr Gln Glu Ala Glu His
545                 550                 555                 560

Gly Ser Phe Arg Val Thr Ser Ser Ser Gln Phe Ser Ser Arg Asp
                565                 570                 575

Ser Ala Gln Leu Ser Asp Ser Gly Ser Ala Asp Glu Val Asp Glu Phe
                580                 585                 590

Glu Ile Gln Asp Ala Asp Ile Arg Arg Asn Thr Ala Ser Ser Ser Lys
            595                 600                 605

Ser Phe Val Ser Ser Gln Ser Phe Ser His Cys Phe Leu His Ser Thr
        610                 615                 620

Ser Ala Glu Ala Val Ala Met Gly Leu Leu Lys Gln Phe Glu Gly Met
625                 630                 635                 640

Gln Leu Pro Ala Ala Ser Glu Leu Glu Trp Leu Val Pro Glu His Asp
                645                 650                 655

Ala Pro Gln Lys Leu Leu Pro Ile Pro Asp Ser Leu Pro Ile Ser Pro
            660                 665                 670

Asp Asp Gly Gln His Ala Asp Ile Tyr Lys Leu Arg Ile Arg Val Arg
        675                 680                 685

Gly Asn Leu Glu Trp Ala Pro Pro Arg Pro Gln Ile Ile Phe Asn Val
        690                 695                 700

His Pro Ala Pro Thr Arg Lys Ile Ala Val Ala Lys Gln Asn Tyr Arg
705                 710                 715                 720

Cys Ala Gly Cys Gly Ile Arg Thr Asp Pro Asp Tyr Ile Lys Arg Leu
                725                 730                 735

Arg Tyr Cys Glu Tyr Leu Gly Lys Tyr Phe Cys Gln Cys Cys His Glu
            740                 745                 750

Asn Ala Gln Met Ala Ile Pro Ser Arg Val Leu Arg Lys Trp Asp Phe
            755                 760                 765

Ser Lys Tyr Tyr Val Ser Asn Phe Ser Lys Asp Leu Leu Ile Lys Ile
        770                 775                 780

Trp Asn Asp Pro Leu Phe Asn Val Gln Asp Ile Asn Ser Ala Leu Tyr
785                 790                 795                 800

Arg Lys Val Lys Leu Leu Asn Gln Val Arg Leu Leu Arg Val Gln Leu
                805                 810                 815
```

```
Cys His Met Lys Asn Met Phe Lys Thr Cys Arg Leu Ala Lys Glu Leu
            820                 825                 830

Leu Asp Ser Phe Asp Thr Val Pro Gly His Leu Thr Glu Asp Leu His
            835                 840                 845

Leu Tyr Ser Leu Asn Asp Leu Thr Ala Thr Arg Lys Gly Glu Leu Gly
            850                 855                 860

Pro Arg Leu Ala Glu Leu Thr Arg Ala Gly Ala Thr His Val Glu Arg
865                 870                 875                 880

Cys Met Leu Cys Gln Ala Lys Gly Phe Ile Cys Glu Phe Cys Gln Asn
                885                 890                 895

Glu Asp Asp Ile Ile Phe Pro Phe Glu Leu His Lys Cys Arg Thr Cys
            900                 905                 910

Glu Glu Cys Lys Ala Cys Tyr His Lys Ala Cys Phe Lys Ser Gly Ser
            915                 920                 925

Cys Pro Arg Cys Glu Arg Leu Gln Ala Arg Glu Ala Leu Ala Arg
            930                 935                 940

Gln Ser Leu Glu Ser Tyr Leu Ser Asp Tyr Glu Glu Pro Ala Glu
945                 950                 955                 960

Ala Leu Ala Leu Glu Ala Ala Val Leu Glu Ala Thr
                965                 970

<210> SEQ ID NO 2
<211> LENGTH: 15
<212> TYPE: PRT
<213> ORGANISM: Artificial Sequence
<220> FEATURE:
<223> OTHER INFORMATION: antigenic peptide
<220> FEATURE:
<221> NAME/KEY: MISC_FEATURE
<222> LOCATION: (5)..(5)
<223> OTHER INFORMATION: Phosphorylated residue

<400> SEQUENCE: 2

Asp Ala His Val Thr Ala Met Leu Gln Cys Leu Glu Ala Val Glu
1               5                   10                  15

<210> SEQ ID NO 3
<211> LENGTH: 2527
<212> TYPE: PRT
<213> ORGANISM: Homo sapiens

<400> SEQUENCE: 3

Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
                20                  25                  30

Glu Thr Leu Val Gln Ile Leu Glu Asp Leu Leu Val Phe Thr Tyr Ser
            35                  40                  45

Glu Arg Ala Ser Lys Leu Phe Gln Gly Lys Asn Ile His Val Pro Leu
        50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125
```

```
Val Asn Leu Ser Val Ile Gly Leu Lys Thr Leu Asp Leu Leu Thr
        130                 135                 140

Ser Gly Lys Ile Thr Leu Ile Leu Asp Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
                180                 185                 190

Glu Glu Gln Leu Thr Glu Phe Val Glu Asn Lys Asp Tyr Met Ile Leu
            195                 200                 205

Leu Ser Ala Leu Thr Asn Phe Lys Asp Glu Glu Ile Val Leu His
210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
                260                 265                 270

Leu Leu His Arg Leu Thr Leu Gly Asn Phe Phe Asn Ile Leu Val Leu
            275                 280                 285

Asn Glu Val His Glu Phe Val Val Lys Ala Val Gln Gln Tyr Pro Glu
290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Asp Lys Leu Phe Trp Leu Glu Ala
            340                 345                 350

Cys Tyr Lys Ala Leu Thr Trp His Arg Lys Asn Lys His Val Gln Glu
            355                 360                 365

Ala Ala Cys Trp Ala Leu Asn Asn Leu Leu Met Tyr Gln Asn Ser Leu
            370                 375                 380

His Glu Lys Ile Gly Asp Glu Asp Gly His Phe Pro Ala His Arg Glu
385                 390                 395                 400

Val Met Leu Ser Met Leu Met His Ser Ser Lys Glu Val Phe Gln
                405                 410                 415

Ala Ser Ala Asn Ala Leu Ser Thr Leu Leu Glu Gln Asn Val Asn Phe
                420                 425                 430

Arg Lys Ile Leu Leu Ser Lys Gly Ile His Leu Asn Val Leu Glu Leu
            435                 440                 445

Met Gln Lys His Ile His Ser Pro Glu Val Ala Glu Ser Gly Cys Lys
            450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
                500                 505                 510

Val Pro Gly Met Pro Glu Glu Ser Arg Glu Asp Thr Glu Phe His His
            515                 520                 525

Lys Leu Asn Met Val Lys Lys Gln Cys Phe Lys Asn Asp Ile His Lys
530                 535                 540
```

-continued

```
Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
        595                 600                 605

Leu Ile Gly Tyr Leu Ile Thr Lys Lys Asn Val Phe Ile Gly Thr Gly
    610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
        675                 680                 685

Gln Gln Phe Leu Asn Leu Cys Cys Lys Cys Phe Ala Lys Val Ala Met
690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Asn Ser Gly Ser Arg Glu
        755                 760                 765

Gln Asp Val Arg Lys Ala Leu Thr Ile Ser Ile Gly Lys Gly Asp Ser
770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
        835                 840                 845

Lys Ser Ala Val Glu Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Ser Asn Ser Ile Ser
            900                 905                 910

Val Gly Glu Phe Tyr Arg Asp Ala Val Leu Gln Arg Cys Ser Pro Asn
        915                 920                 925

Leu Gln Arg His Ser Asn Ser Leu Gly Pro Ile Phe Asp His Glu Asp
930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
```

```
            965                 970                 975
Leu Ala Ser Glu Arg Glu Tyr Ile Thr Ser Leu Asp Leu Ser Ala Asn
                980                 985                 990
Glu Leu Arg Asp Ile Asp Ala Leu  Ser Gln Lys Cys Cys Ile Ser Val
            995                 1000                1005
His Leu  Glu His Leu Glu Lys  Leu Glu Leu His Gln  Asn Ala Leu
    1010                1015                1020
Thr Ser  Phe Pro Gln Gln Leu  Cys Glu Thr Leu Lys  Ser Leu Thr
    1025                1030                1035
His Leu Asp Leu His Ser Asn Lys Phe Thr Ser Phe Pro Ser Tyr
    1040                1045                1050
Leu Leu Lys Met Ser Cys Ile Ala Asn Leu Asp Val Ser Arg Asn
    1055                1060                1065
Asp Ile Gly Pro Ser Val Val Leu Asp Pro Thr Val Lys Cys Pro
    1070                1075                1080
Thr Leu Lys Gln Phe Asn Leu Ser Tyr Asn Gln Leu Ser Phe Val
    1085                1090                1095
Pro Glu Asn Leu Thr Asp Val Val Glu Lys Leu Glu Gln Leu Ile
    1100                1105                1110
Leu Glu Gly Asn Lys Ile Ser Gly Ile Cys Ser Pro Leu Arg Leu
    1115                1120                1125
Lys Glu Leu Lys Ile Leu Asn Leu Ser Lys Asn His Ile Ser Ser
    1130                1135                1140
Leu Ser Glu Asn Phe Leu Glu Ala Cys Pro Lys Val Glu Ser Phe
    1145                1150                1155
Ser Ala Arg Met Asn Phe Leu Ala Ala Met Pro Phe Leu Pro Pro
    1160                1165                1170
Ser Met Thr Ile Leu Lys Leu Ser Gln Asn Lys Phe Ser Cys Ile
    1175                1180                1185
Pro Glu Ala Ile Leu Asn Leu Pro His Leu Arg Ser Leu Asp Met
    1190                1195                1200
Ser Ser Asn Asp Ile Gln Tyr Leu Pro Gly Pro Ala His Trp Lys
    1205                1210                1215
Ser Leu Asn Leu Arg Glu Leu Leu Phe Ser His Asn Gln Ile Ser
    1220                1225                1230
Ile Leu Asp Leu Ser Glu Lys Ala Tyr Leu Trp Ser Arg Val Glu
    1235                1240                1245
Lys Leu His Leu Ser His Asn Lys Leu Lys Glu Ile Pro Pro Glu
    1250                1255                1260
Ile Gly Cys Leu Glu Asn Leu Thr Ser Leu Asp Val Ser Tyr Asn
    1265                1270                1275
Leu Glu Leu Arg Ser Phe Pro Asn Glu Met Gly Lys Leu Ser Lys
    1280                1285                1290
Ile Trp Asp Leu Pro Leu Asp Glu Leu His Leu Asn Phe Asp Phe
    1295                1300                1305
Lys His Ile Gly Cys Lys Ala Lys Asp Ile Ile Arg Phe Leu Gln
    1310                1315                1320
Gln Arg Leu Lys Lys Ala Val Pro Tyr Asn Arg Met Lys Leu Met
    1325                1330                1335
Ile Val Gly Asn Thr Gly Ser Gly Lys Thr Thr Leu Leu Gln Gln
    1340                1345                1350
Leu Met Lys Thr Lys Lys Ser Asp Leu Gly Met Gln Ser Ala Thr
    1355                1360                1365
```

```
Val Gly Ile Asp Val Lys Asp Trp Pro Ile Gln Ile Arg Asp Lys
1370            1375                1380

Arg Lys Arg Asp Leu Val Leu Asn Val Trp Asp Phe Ala Gly Arg
1385            1390                1395

Glu Glu Phe Tyr Ser Thr His Pro His Phe Met Thr Gln Arg Ala
1400            1405                1410

Leu Tyr Leu Ala Val Tyr Asp Leu Ser Lys Gly Gln Ala Glu Val
1415            1420                1425

Asp Ala Met Lys Pro Trp Leu Phe Asn Ile Lys Ala Arg Ala Ser
1430            1435                1440

Ser Ser Pro Val Ile Leu Val Gly Thr His Leu Asp Val Ser Asp
1445            1450                1455

Glu Lys Gln Arg Lys Ala Cys Met Ser Lys Ile Thr Lys Glu Leu
1460            1465                1470

Leu Asn Lys Arg Gly Phe Pro Ala Ile Arg Asp Tyr His Phe Val
1475            1480                1485

Asn Ala Thr Glu Glu Ser Asp Ala Leu Ala Lys Leu Arg Lys Thr
1490            1495                1500

Ile Ile Asn Glu Ser Leu Asn Phe Lys Ile Arg Asp Gln Leu Val
1505            1510                1515

Val Gly Gln Leu Ile Pro Asp Cys Tyr Val Glu Leu Glu Lys Ile
1520            1525                1530

Ile Leu Ser Glu Arg Lys Asn Val Pro Ile Glu Phe Pro Val Ile
1535            1540                1545

Asp Arg Lys Arg Leu Leu Gln Leu Val Arg Glu Asn Gln Leu Gln
1550            1555                1560

Leu Asp Glu Asn Glu Leu Pro His Ala Val His Phe Leu Asn Glu
1565            1570                1575

Ser Gly Val Leu Leu His Phe Gln Asp Pro Ala Leu Gln Leu Ser
1580            1585                1590

Asp Leu Tyr Phe Val Glu Pro Lys Trp Leu Cys Lys Ile Met Ala
1595            1600                1605

Gln Ile Leu Thr Val Lys Val Glu Gly Cys Pro Lys His Pro Lys
1610            1615                1620

Gly Ile Ile Ser Arg Arg Asp Val Glu Lys Phe Leu Ser Lys Lys
1625            1630                1635

Arg Lys Phe Pro Lys Asn Tyr Met Ser Gln Tyr Phe Lys Leu Leu
1640            1645                1650

Glu Lys Phe Gln Ile Ala Leu Pro Ile Gly Glu Glu Tyr Leu Leu
1655            1660                1665

Val Pro Ser Ser Leu Ser Asp His Arg Pro Val Ile Glu Leu Pro
1670            1675                1680

His Cys Glu Asn Ser Glu Ile Ile Ile Arg Leu Tyr Glu Met Pro
1685            1690                1695

Tyr Phe Pro Met Gly Phe Trp Ser Arg Leu Ile Asn Arg Leu Leu
1700            1705                1710

Glu Ile Ser Pro Tyr Met Leu Ser Gly Arg Glu Arg Ala Leu Arg
1715            1720                1725

Pro Asn Arg Met Tyr Trp Arg Gln Gly Ile Tyr Leu Asn Trp Ser
1730            1735                1740

Pro Glu Ala Tyr Cys Leu Val Gly Ser Glu Val Leu Asp Asn His
1745            1750                1755
```

```
Pro Glu Ser Phe Leu Lys Ile Thr Val Pro Ser Cys Arg Lys Gly
    1760            1765                1770

Cys Ile Leu Leu Gly Gln Val Val Asp His Ile Asp Ser Leu Met
    1775            1780                1785

Glu Glu Trp Phe Pro Gly Leu Leu Glu Ile Asp Ile Cys Gly Glu
    1790            1795                1800

Gly Glu Thr Leu Leu Lys Lys Trp Ala Leu Tyr Ser Phe Asn Asp
    1805            1810                1815

Gly Glu Glu His Gln Lys Ile Leu Leu Asp Asp Leu Met Lys Lys
    1820            1825                1830

Ala Glu Glu Gly Asp Leu Leu Val Asn Pro Asp Gln Pro Arg Leu
    1835            1840                1845

Thr Ile Pro Ile Ser Gln Ile Ala Pro Asp Leu Ile Leu Ala Asp
    1850            1855                1860

Leu Pro Arg Asn Ile Met Leu Asn Asn Asp Glu Leu Glu Phe Glu
    1865            1870                1875

Gln Ala Pro Glu Phe Leu Leu Gly Asp Gly Ser Phe Gly Ser Val
    1880            1885                1890

Tyr Arg Ala Ala Tyr Glu Gly Glu Glu Val Ala Val Lys Ile Phe
    1895            1900                1905

Asn Lys His Thr Ser Leu Arg Leu Leu Arg Gln Glu Leu Val Val
    1910            1915                1920

Leu Cys His Leu His His Pro Ser Leu Ile Ser Leu Leu Ala Ala
    1925            1930                1935

Gly Ile Arg Pro Arg Met Leu Val Met Glu Leu Ala Ser Lys Gly
    1940            1945                1950

Ser Leu Asp Arg Leu Leu Gln Gln Asp Lys Ala Ser Leu Thr Arg
    1955            1960                1965

Thr Leu Gln His Arg Ile Ala Leu His Val Ala Asp Gly Leu Arg
    1970            1975                1980

Tyr Leu His Ser Ala Met Ile Ile Tyr Arg Asp Leu Lys Pro His
    1985            1990                1995

Asn Val Leu Leu Phe Thr Leu Tyr Pro Asn Ala Ala Ile Ile Ala
    2000            2005                2010

Lys Ile Ala Asp Tyr Gly Ile Ala Gln Tyr Cys Cys Arg Met Gly
    2015            2020                2025

Ile Lys Thr Ser Glu Gly Thr Pro Gly Phe Arg Ala Pro Glu Val
    2030            2035                2040

Ala Arg Gly Asn Val Ile Tyr Asn Gln Gln Ala Asp Val Tyr Ser
    2045            2050                2055

Phe Gly Leu Leu Leu Tyr Asp Ile Leu Thr Thr Gly Gly Arg Ile
    2060            2065                2070

Val Glu Gly Leu Lys Phe Pro Asn Glu Phe Asp Glu Leu Glu Ile
    2075            2080                2085

Gln Gly Lys Leu Pro Asp Pro Val Lys Glu Tyr Gly Cys Ala Pro
    2090            2095                2100

Trp Pro Met Val Glu Lys Leu Ile Lys Gln Cys Leu Lys Glu Asn
    2105            2110                2115

Pro Gln Glu Arg Pro Thr Ser Ala Gln Val Phe Asp Ile Leu Asn
    2120            2125                2130

Ser Ala Glu Leu Val Cys Leu Thr Arg Arg Ile Leu Leu Pro Lys
    2135            2140                2145

Asn Val Ile Val Glu Cys Met Val Ala Thr His His Asn Ser Arg
```

```
                2150                2155                2160
Asn Ala Ser Ile Trp Leu Gly Cys Gly His Thr Asp Arg Gly Gln
    2165                2170                2175
Leu Ser Phe Leu Asp Leu Asn Thr Glu Gly Tyr Thr Ser Glu Glu
    2180                2185                2190
Val Ala Asp Ser Arg Ile Leu Cys Leu Ala Leu Val His Leu Pro
    2195                2200                2205
Val Glu Lys Glu Ser Trp Ile Val Ser Gly Thr Gln Ser Gly Thr
    2210                2215                2220
Leu Leu Val Ile Asn Thr Glu Asp Gly Lys Lys Arg His Thr Leu
    2225                2230                2235
Glu Lys Met Thr Asp Ser Val Thr Cys Leu Tyr Cys Asn Ser Phe
    2240                2245                2250
Ser Lys Gln Ser Lys Gln Lys Asn Phe Leu Leu Val Gly Thr Ala
    2255                2260                2265
Asp Gly Lys Leu Ala Ile Phe Glu Asp Lys Thr Val Lys Leu Lys
    2270                2275                2280
Gly Ala Ala Pro Leu Lys Ile Leu Asn Ile Gly Asn Val Ser Thr
    2285                2290                2295
Pro Leu Met Cys Leu Ser Glu Ser Thr Asn Ser Thr Glu Arg Asn
    2300                2305                2310
Val Met Trp Gly Gly Cys Gly Thr Lys Ile Phe Ser Phe Ser Asn
    2315                2320                2325
Asp Phe Thr Ile Gln Lys Leu Ile Glu Thr Arg Thr Ser Gln Leu
    2330                2335                2340
Phe Ser Tyr Ala Ala Phe Ser Asp Ser Asn Ile Ile Thr Val Val
    2345                2350                2355
Val Asp Thr Ala Leu Tyr Ile Ala Lys Gln Asn Ser Pro Val Val
    2360                2365                2370
Glu Val Trp Asp Lys Lys Thr Glu Lys Leu Cys Gly Leu Ile Asp
    2375                2380                2385
Cys Val His Phe Leu Arg Glu Val Met Val Lys Glu Asn Lys Glu
    2390                2395                2400
Ser Lys His Lys Met Ser Tyr Ser Gly Arg Val Lys Thr Leu Cys
    2405                2410                2415
Leu Gln Lys Asn Thr Ala Leu Trp Ile Gly Thr Gly Gly Gly His
    2420                2425                2430
Ile Leu Leu Leu Asp Leu Ser Thr Arg Arg Leu Ile Arg Val Ile
    2435                2440                2445
Tyr Asn Phe Cys Asn Ser Val Arg Val Met Met Thr Ala Gln Leu
    2450                2455                2460
Gly Ser Leu Lys Asn Val Met Leu Val Leu Gly Tyr Asn Arg Lys
    2465                2470                2475
Asn Thr Glu Gly Thr Gln Lys Gln Lys Glu Ile Gln Ser Cys Leu
    2480                2485                2490
Thr Val Trp Asp Ile Asn Leu Pro His Glu Val Gln Asn Leu Glu
    2495                2500                2505
Lys His Ile Glu Val Arg Lys Glu Leu Ala Glu Lys Met Arg Arg
    2510                2515                2520
Thr Ser Val Glu
    2525

<210> SEQ ID NO 4
```

```
<211> LENGTH: 16
<212> TYPE: PRT
<213> ORGANISM: Artificial Sequence
<220> FEATURE:
<223> OTHER INFORMATION: LC-CDR1

<400> SEQUENCE: 4

Arg Ser Ser Gln Ser Leu Val His Ser Asn Gly Asn Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: LC-CDR2

<400> SEQUENCE: 5

Lys Leu Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LC-CDR3

<400> SEQUENCE: 6

Ser Gln Ser Thr His Val Pro Leu Thr
1               5

<210> SEQ ID NO 7
<211> LENGTH: 5
<212> TYPE: PRT
<213> ORGANISM: Artificial Sequence
<220> FEATURE:
<223> OTHER INFORMATION: HC-CDR1

<400> SEQUENCE: 7

Asn Tyr Gly Val Ser
1               5

<210> SEQ ID NO 8
<211> LENGTH: 17
<212> TYPE: PRT
<213> ORGANISM: Artificial Sequence
<220> FEATURE:
<223> OTHER INFORMATION: HC-CDR2

<400> SEQUENCE: 8

Thr Ile Asn Ser Asn Gly Gly Ser Lys Tyr Tyr Pro Asp Ser Val Lys
1               5                   10                  15

Gly

<210> SEQ ID NO 9
<211> LENGTH: 12
<212> TYPE: PRT
<213> ORGANISM: Artificial Sequence
<220> FEATURE:
<223> OTHER INFORMATION: HC-CDR3

<400> SEQUENCE: 9

Asp Val Trp Leu Arg Arg Gln Trp Tyr Phe Asp Val
1               5                   10
```

<210> SEQ ID NO 10
<211> LENGTH: 420
<212> TYPE: DNA
<213> ORGANISM: Artificial Sequence
<220> FEATURE:
<223> OTHER INFORMATION: Heavy Chain

<400> SEQUENCE: 10

```
atgaacttag ggctcagctt cattttcctt gcccttattt taaaaggtgt ccagtgtgag    60
gtgcagctgg tggagtctgg gggaggctta gtgcagcctg agggtccct gaaactctcc    120
tgtgcagcct ctggattcac tttcactaat tatggcgtgt cttgggttcg ccagactcca   180
gacaagaggc tggagttggt cgcaaccatt aatagtaatg gtggtagtaa atattatcca   240
gacagtgtga agggccgatt caccatttcc agagacactg ccaagaacac cctgtacctg   300
catatgagca gtctgaagtc tgaggacaca gccatgtatt actgtgcaag agatgtatgg   360
ttacgacgtc agtggtactt cgatgtctgg ggcgcaggga ccacggtcac cgtctcctca   420
```

<210> SEQ ID NO 11
<211> LENGTH: 393
<212> TYPE: DNA
<213> ORGANISM: Artificial Sequence
<220> FEATURE:
<223> OTHER INFORMATION: Light chain

<400> SEQUENCE: 11

```
atgaagttgc ctgttaggct gttggtgctg atgttctgga ttcctgcttc cagcagtgat    60
gttgtgatga cccaaactcc ctctcccctg cctgtcagtc ttggagatcc agcctccatc   120
tcttgcagat ctagtcagag ccttgtacac agtaatggaa acacctattt acattggtac   180
ctgcagaaga caggccagtc tccaaagctc ctgatctaca aactttccaa ccgattttct   240
ggggtcccag acaggttcag tggcagtgga tcagggacag atttcacact caagatcagc   300
agagtggagg ctgaggatct gggagtttat ttctgctctc aaagtacaca tgttcctctc   360
acgttcggtg ctgggaccaa gctggagctg aaa                                 393
```

<210> SEQ ID NO 12
<211> LENGTH: 131
<212> TYPE: PRT
<213> ORGANISM: Artificial Sequence
<220> FEATURE:
<223> OTHER INFORMATION: Light chain

<400> SEQUENCE: 12

```
Met Lys Leu Pro Val Arg Leu Leu Val Leu Met Phe Trp Ile Pro Ala
 1               5                  10                  15

Ser Ser Ser Asp Val Val Met Thr Gln Thr Pro Leu Ser Leu Pro Val
            20                  25                  30

Ser Leu Gly Asp Pro Ala Ser Ile Ser Cys Arg Ser Ser Gln Ser Leu
        35                  40                  45

Val His Ser Asn Gly Asn Thr Tyr Leu His Trp Tyr Leu Gln Lys Thr
    50                  55                  60

Gly Gln Ser Pro Lys Leu Leu Ile Tyr Lys Leu Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Leu Thr Phe Gly Ala Gly Thr Lys Leu
```

```
                   115                 120                 125
Glu Leu Lys
   130

<210> SEQ ID NO 13
<211> LENGTH: 140
<212> TYPE: PRT
<213> ORGANISM: Artificial Sequence
<220> FEATURE:
<223> OTHER INFORMATION: heavy chain

<400> SEQUENCE: 13

Met Asn Leu Gly Leu Ser Phe Ile Phe Leu Ala Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Thr Asn Tyr Gly Val Ser Trp Val Arg Gln Thr Pro Asp Lys Arg Leu
    50                  55                  60

Glu Leu Val Ala Thr Ile Asn Ser Asn Gly Gly Ser Lys Tyr Tyr Pro
65                  70                  75                  80

Asp Ser Val Lys Gly Arg Phe Thr Ile Ser Arg Asp Thr Ala Lys Asn
                85                  90                  95

Thr Leu Tyr Leu His Met Ser Ser Leu Lys Ser Glu Asp Thr Ala Met
            100                 105                 110

Tyr Tyr Cys Ala Arg Asp Val Trp Leu Arg Arg Gln Trp Tyr Phe Asp
        115                 120                 125

Val Trp Gly Ala Gly Thr Thr Val Thr Val Ser Ser
    130                 135                 140

<210> SEQ ID NO 14
<211> LENGTH: 15
<212> TYPE: PRT
<213> ORGANISM: Artificial Sequence
<220> FEATURE:
<223> OTHER INFORMATION: un-phosphorylated antigen

<400> SEQUENCE: 14

Asp Ala His Val Thr Ala Met Leu Gln Cys Leu Glu Ala Val Glu
1               5                   10                  15
```